United States Patent
Madabhushi et al.

(10) Patent No.: US 10,970,838 B2
(45) Date of Patent: Apr. 6, 2021

(54) HOUGH TRANSFORM-BASED VASCULAR NETWORK DISORDER FEATURES ON BASELINE FLUORESCEIN ANGIOGRAPHY SCANS PREDICT RESPONSE TO ANTI-VEGF THERAPY IN DIABETIC MACULAR EDEMA

(71) Applicants: Case Western Reserve University, Cleveland, OH (US); The Cleveland Clinic Foundation, Cleveland, OH (US)

(72) Inventors: Anant Madabhushi, Shaker Heights, OH (US); Prateek Prasanna, Cleveland, OH (US); Justis Ehlers, Cleveland, OH (US); Sunil Srivastava, Cleveland, OH (US)

(73) Assignees: Case Western Reserve University, Cleveland, OH (US); The Cleveland Clinic Foundation, Cleveland, OH (US)

(*) Notice: Subject to any disclaimer, the term of this patent is extended or adjusted under 35 U.S.C. 154(b) by 152 days.

(21) Appl. No.: 16/415,184

(22) Filed: May 17, 2019

(65) Prior Publication Data
US 2020/0027208 A1 Jan. 23, 2020

Related U.S. Application Data

(60) Provisional application No. 62/699,862, filed on Jul. 18, 2018.

(51) Int. Cl.
*G06T 7/00* (2017.01)
*G06T 5/50* (2006.01)
(Continued)

(52) U.S. Cl.
CPC ........ *G06T 7/0012* (2013.01); *G06K 9/00147* (2013.01); *G06T 5/50* (2013.01);
(Continued)

(58) Field of Classification Search
CPC ............... G06T 7/0012; G06T 5/50; G06T 2207/30104; G06T 2207/20061;
(Continued)

(56) References Cited

U.S. PATENT DOCUMENTS

2010/0104168 A1* 4/2010 Dobbe ............... G06T 7/60
382/134
2010/0172568 A1* 7/2010 Malon ............... G06T 7/0012
382/133

(Continued)

*Primary Examiner* — Amandeep Saini
(74) *Attorney, Agent, or Firm* — Eschweiler & Potashnik, LLC

(57) ABSTRACT

Embodiments facilitate prediction of anti-vascular endothelial growth (anti-VEGF) therapy response in DME or RVO patients. A first set of embodiments discussed herein relates to training of a machine learning classifier to determine a prediction for response to anti-VEGF therapy based on a vascular network organization via Hough transform (VaNgOGH) descriptor generated based on FA images of tissue demonstrating DME or RVO. A second set of embodiments discussed herein relates to determination of a prediction of response to anti-VEGF therapy for a DME or RVO patient (e.g., non-rebounder vs. rebounder, response vs. non-response) based on a VaNgOGH descriptor generated based on FA imagery of the patient.

20 Claims, 10 Drawing Sheets

(51) Int. Cl.
*G16H 30/20* (2018.01)
*G16H 30/40* (2018.01)
*G16H 50/30* (2018.01)
*G06K 9/00* (2006.01)
G16B 50/30 (2019.01)

(52) U.S. Cl.
CPC ............ *G16H 30/20* (2018.01); *G16H 30/40* (2018.01); *G16H 50/30* (2018.01); *G01N 2800/2871* (2013.01); *G01N 2800/324* (2013.01); *G01N 2800/347* (2013.01); *G06T 2207/20061* (2013.01); *G06T 2207/30104* (2013.01); *G16B 50/30* (2019.02)

(58) Field of Classification Search
CPC . G06T 2207/30101; G06T 7/12; G16H 30/20; G16H 30/40; G16H 50/30; G16H 50/20; G16H 20/00; G06K 9/00147; G06K 9/4609; G06K 2209/05; G01N 2800/324; G01N 2800/2871; G01N 2800/347; G16B 50/30
USPC .......................................................... 382/128
See application file for complete search history.

(56) References Cited

U.S. PATENT DOCUMENTS

2015/0110368 A1* 4/2015 Solanki .................... A61B 3/14
  382/128
2019/0287243 A1* 9/2019 Madabhushi ........ G06K 9/6286

\* cited by examiner

HOUGH TRANSFORM-BASED VASCULAR NETWORK DISORDER FEATURES ON BASELINE FLUORESCEIN ANGIOGRAPHY SCANS PREDICT RESPONSE TO ANTI-VEGF THERAPY IN DIABETIC MACULAR EDEMA

CROSS REFERENCE TO RELATED APPLICATIONS

This application claims the benefit of U.S. Provisional Application 62/699,862 filed Jul. 18, 2018, which is incorporated by reference herein in its entirety.

FEDERAL FUNDING NOTICE

This invention was made with government support under the grant(s) CA199374, CA202752, CA208236, EY022947, and RR012463 awarded by the National Institutes of Health. Also grants W81XWH-18-1-0404, W81XWH-13-1-0418, and W81XWH-14-1-0323 awarded by the Department of Defense. The government has certain rights in the invention.

BACKGROUND

Diabetic macular edema (DME) is one of the leading causes of vision loss in patients with diabetic mellitus. The major cause of DME-related vision loss is the disruption in the blood-retinal barrier, which leads to fluid accumulation within intra-retinal layers of the macula. When evaluating DME, fluorescein angiography (FA) provides information on vascular leakage and non-perfusion. The use of ultra-wide FA (UWFA) is becoming more common given its ability to provide near panretinal assessment of disease burden. A rise in vascular endothelial growth factor (VEGF) is linked to an increase in permeability in the blood-retinal barrier, thereby initiating a cascade of events which ultimately leads to a loss in visual acuity.

Anti-VEGF therapy has emerged as a first-line treatment for DME. Utilization of anti-VEGF therapy has improved clinical outcomes by improving visual acuity and reducing macular edema. While these outcomes do present promising results for the future, there still lies a void in the knowledge surrounding the impact of anti-VEGF treatment on the underlying pathology of retinal vasculature characteristics, such as blood-vessel arrangement, vascular leakage, and ischemia. In addition, discriminating image features that may be important biomarkers for treatment response have not been identified by existing approaches. Furthermore, existing approaches to UWFA interpretation rely on subjective physician interpretation, and quantitative higher-order assessment is not readily available in clinical situations.

BRIEF DESCRIPTION OF THE DRAWINGS

The accompanying drawings, which are incorporated in and constitute a part of the specification, illustrate various example operations, apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Diabetes-induced vascular disruption results in hypoxia leading to upregulation of vascular endothelial growth factor (VEGF) and increased vascular permeability. VEGF then produces conformational changes in tight junctions of retinal vascular endothelial cells. This may lead to tortuosity changes in the vascular network. A statistically significant dilation and elongation of retinal arterioles, venules, and their macular branches may be found before a diagnosis of macular edema in a patient. Embodiments quantify differences in vascular phenotypes of non-rebounders and rebounders. Embodiments leverage quantification of features of vessel arrangement for improved anti-VEGF therapy response prediction. Embodiments quantify differences in vessel network disorder across patients to facilitate improved identification of candidates for anti-VEGF treatment.

Embodiments employ a vascular network organization via Hough transform (VaNgOGH) image-based descriptor to model the architectural disorder of the retinal vascular network on baseline (e.g., pre-anti-VEGF treatment) fluorescein angiography (FA) scans of patients who may be subsequently treated with anti-VEGF injection (e.g., Aflibercept). Embodiments employing VaNgOGH compute local measures of vessel-curvature in the Hough parameter space. Using localized Hough transforms, embodiments employing VaNgOGH identify dominant peaks in the accumulator space. Embodiments determine differences in VaNgOGH features between eyes that tolerate extended dosing intervals (non-rebounders) compared to eyes that do not tolerate extended dosing intervals (rebounders). Embodiments may demonstrate differences in VaNgOGH features between eyes that tolerate extended dosing intervals compared to eyes that do not using statistical significance tests or box and whisker plots. Embodiments employ VaNgOGH in conjunction with a machine learning classifier to distinguish a first category (e.g., non-rebounders, eyes that tolerate extended dosing intervals) from a second, different category (e.g., rebounders, eyes that do not tolerate extended dosing intervals).

Figure 1:
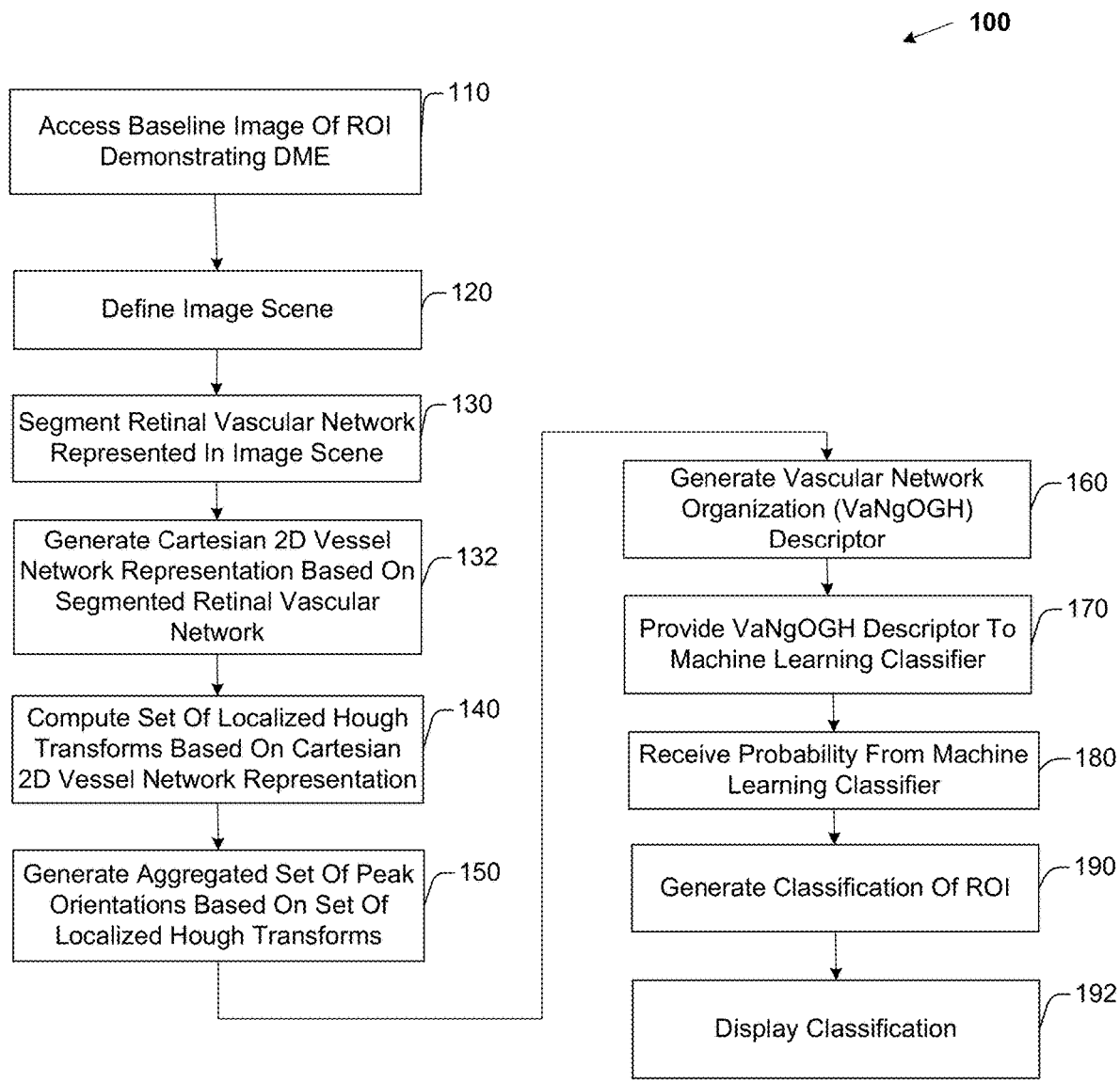
FIG. 1 is a flow diagram of example methodology or operations for distinguishing non-rebounders from rebounders based on the architectural disorder of a vascular architecture associated with diabetic macular edema (DME) or retinal vein occlusion (RVO) according to various embodiments described herein.

FIG. 1 is a flow diagram of a methodology or set of operations 100 for distinguishing eyes that will exhibit favorable response to extended interval Aflibercept dosing (non-rebounders) from eyes that require more frequent dosing (rebounders). Operations 100 may be performed by a processor. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

Operations 100 includes, at 110, accessing a two-dimensional (2D) fluorescein angiography (FA) image of a region of interest (ROI). The ROI demonstrates diabetic macular edema (DME). In one embodiment, the ROI demonstrates retinal vein occlusion (RVO). The ROI includes a retinal vasculature. The 2D FA image includes a plurality of pixels, a pixel having an intensity. In one embodiment, the 2D FA image is a baseline (e.g., pre-anti-VEGF treatment) ultra-wide field FA (UWFA) image. Embodiments employing UWFA imagery facilitate acquisition of an image that includes a simultaneous pole to periphery view of the retina. This allows the entire retinal vasculature to be imaged during the dye transit by a non-contact method, which further facilitates segmenting the retinal vasculature. In one embodiment, an Optos 200Tx scanner is used to obtain the UWFA image. Accessing the 2D FA image includes acquiring electronic data, reading from a computer file, receiving a computer file, reading from a computer memory, or other computerized activity not practically performed in a human mind.

Operations 100 also includes, at 120, defining an image scene based on the 2D FA image. The image scene includes a representation of the retinal vascular network. In one embodiment, defining the image scene includes defining the image scene I as I=(C,f), where I is a spatial grid C of pixels c∈C in a two-dimensional (2D) space $\mathbb{R}^2$. Each pixel, c∈C, is associated with an intensity value f(c). Defining the image scene includes acquiring electronic data, reading from a computer file, receiving a computer file, reading from a computer memory, or other computerized activity not practically performed in a human mind.

Operations 100 also includes, at 130, segmenting the retinal vascular network represented in the image scene. Segmenting the retinal vascular network includes segmenting blood vessels represented in the image. Segmenting the retinal vascular network may include segmenting blood vessels represented in the image using an automated vessel, leakage, and microaneurysm segmentation approach. Embodiments may employ a morphological-based segmentation technique, or may employ a deep learning model for segmenting the retinal vascular network. One suitable automated segmentation approach is described in Ehlers, J. P., Wang, K., Vasanji, A., Hu, M., and Srivastava, S. K., "Automated quantitative characterization of retinal vascular leakage and microaneurysms in ultra-wide field fluorescein angiography," *British Journal of Ophthalmology* 101(6), 696-699 (2017). Other automated segmentation techniques may be employed. In one embodiment, operations 100 may further include, at 130, generating a panretinal vascular skeletonized map, a leakage localization mask, and a microaneurysm mask based on the 2D FA image. In one embodiment, operations 100 may further include, at 130, correcting the 2D FA image (e.g., UWFA) for warping by processing the 2D FA image using a dewarping transformation technique. One suitable dewarping transformation technique is described in Croft D. E., van Hemert Wykoff C. C., et al. "Precise Montaging and Metric Quantification of Retinal Surface Area From Ultra-Widefield Fundus Photography and Fluorescein Angiography," *Ophthalmic Surgery, Lasers Imaging Retin.* 2014:45(4):312-317. doi:10.3928/23258160-20140709-07. Other dewarping transformation techniques may be employed.

Operations 100 also includes, at 132, generating a Cartesian 2D vessel network representation in the Cartesian domain based on the segmented retinal vascular network. In one embodiment, generating the Cartesian 2D vessel network representation includes computing a centerline of a vessel of the retinal vascular network. In this embodiment, generating the Cartesian 2D vessel network representation further includes generating a skeleton S of the retinal vascular network, where S comprises a series of points in 2D Cartesian space. In one embodiment, $V_{xy}$ depicts the Cartesian 2D retinal vascular network in the image plane (e.g., x,y plane). In one embodiment, generating the Cartesian 2D vessel network representation includes generating a 2D representation of S in the XY plane. Generating the Cartesian 2D vessel network representation includes acquiring electronic data, reading from a computer file, receiving a computer file, reading from a computer memory, or other computerized activity not practically performed in a human mind.

Operations 100 also includes, at 140, computing a set of localized Hough transforms based on the Cartesian 2D vessel network representation. In one embodiment, computing the set of localized Hough transforms includes, for an N pixel by N pixel sliding window W with an offset of k pixels, mapping each pixel in the 2D representation of S in the XY plane to an accumulator space using a Hough transform of the 2D representation of S in the XY plane into polar co-ordinates (ρ,θ), such that for each point in the medial axis skeleton S there exists a unique sinusoid in the accumulator space. In various embodiments described herein, the equation of a line is represented by $$y = \left(-\frac{\cos\theta}{\sin\theta}\right)x + \left(\frac{\rho}{\sin\theta}\right).$$

In this embodiment, computing the set of localized Hough transforms also includes identifying the top five grid locations accumulating the most sinusoid crossings for each window W N and k are positive integers. In one embodiment, N=10 and k=3. In another embodiment, N or k may have other, different values, or may be user definable.

Figure 5:
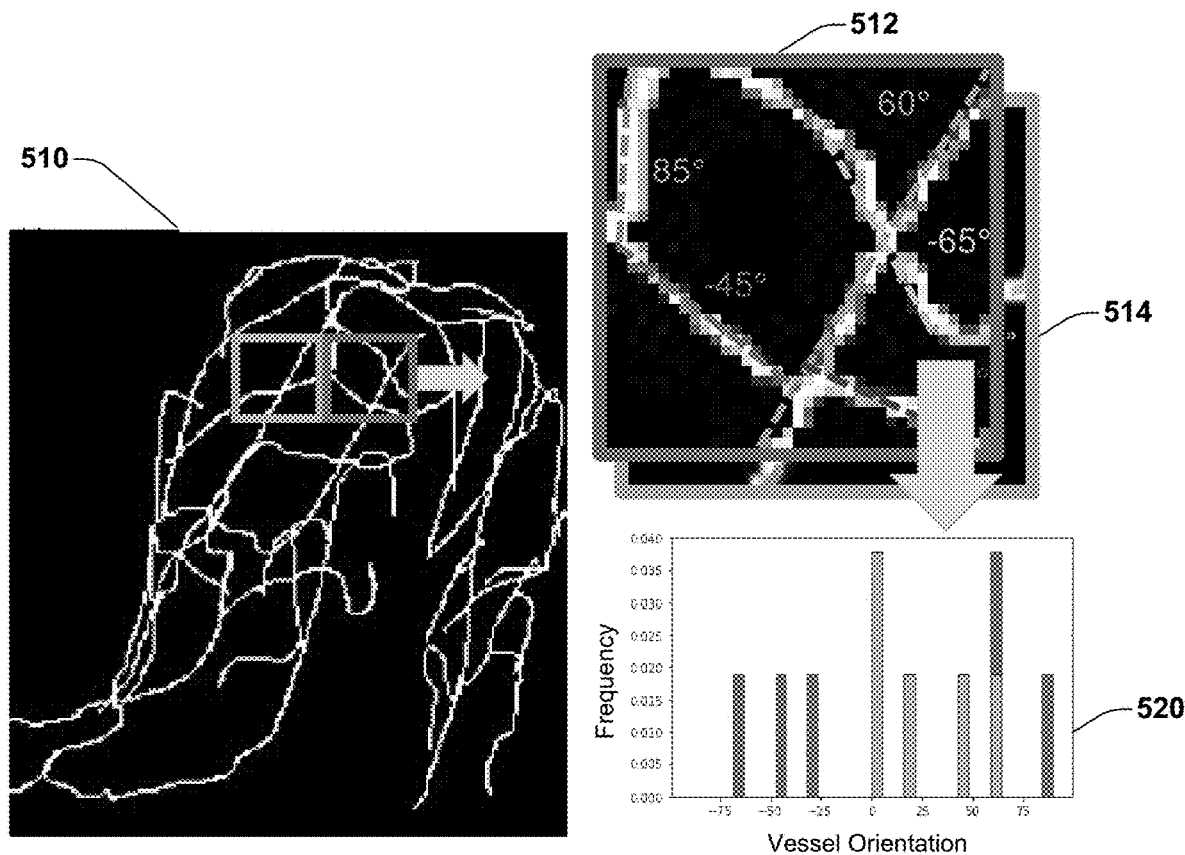
FIG. 5 illustrates a sliding window for analysis of local vessel orientation.
Figure 6:
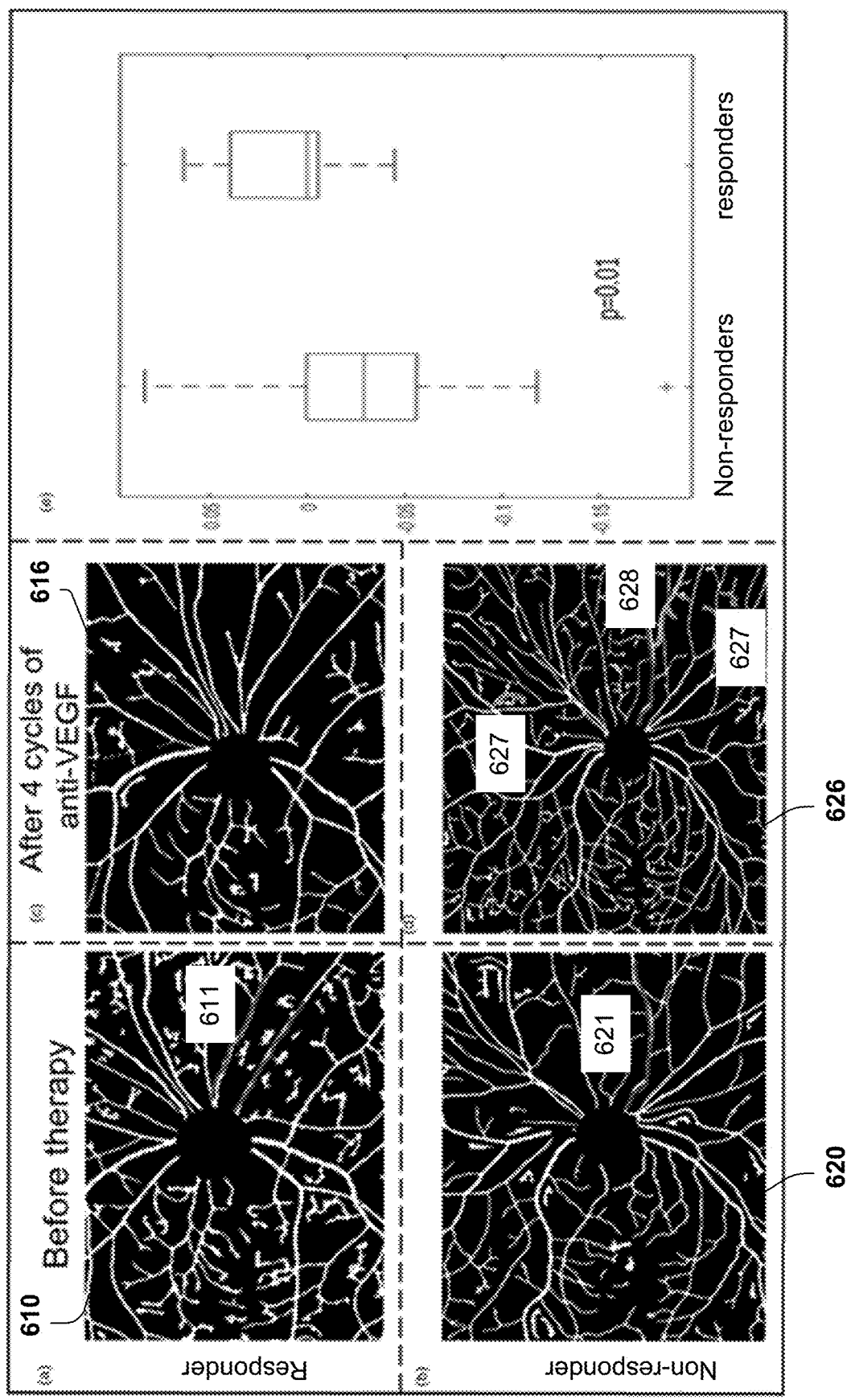
FIG. 6 illustrates primary, secondary, and tertiary blood vessels in UWFA imagery.

FIG. 5 illustrates an exemplary sliding window 510. Instances of vasculature captured by sliding window 510 are illustrated at 512 and 514. Graph 520 indicates frequency of vessel orientation as captured by the instances of sliding window 510 illustrated at 512 and 514, according to various embodiments described herein. Computing the set of localized Hough transforms based on the Cartesian 2D vessel network representation, including mapping the Cartesian 2D retinal vascular network to an accumulator space, includes acquiring electronic data, reading from a computer file, receiving a computer file, reading from a computer memory, or other computerized activity not practically performed in a human mind.

Operations 100 also includes, at 150, generating an aggregated set of peak orientations based on the set of localized Hough transforms. In one embodiment, generating the aggregated set of peak orientations based on the set of localized Hough transforms includes computing a feature set $F_{xy}$ comprising the θ values associated with the five most prominent peak orientations such that $F_{xy}=[\theta_1, \theta_2, \ldots \theta_5]$. While five grid locations are described in this embodiment, in other embodiments, another, different number M (e.g., 3, 7) of grid locations or most prominent peak orientations may be employed. In various embodiments, M may be user adjustable. Thus, in another embodiment, feature set $F_{xy}$ may comprise the θ values associated with the M most prominent peak orientations such that such that, $F_{xy}=[\theta_1, \theta_2, \ldots \theta_M]$.

Operations 100 also includes, at 160, generating a vascular network organization via Hough transform (VaNgOGH) descriptor based on the aggregated set of peak orientations. In one embodiment, the VaNgOGH descriptor is defined as $F_V$. In this embodiment, the VaNgOGH descriptor $F_V$, is generated as a concatenation of the first order statistics, mean, median, standard deviation, skewness, and kurtosis, computed based on $F_{xy}$. In one embodiment, the VaNgOGH descriptor $F_V$, is a 25 by 1 feature vector. Generating the vascular network organization descriptor (e.g., VaNgOGH descriptor) includes acquiring electronic data, reading from a computer file, receiving a computer file, reading from a computer memory, or other computerized activity not practically performed in a human mind.

Operations 100 also includes, at 170, providing the VaNgOGH descriptor to a machine learning classifier configured to compute a probability that the ROI is a non-rebounder. In one embodiment, a non-rebounder is defined as a favorable responder to anti-VEGF therapy after at least three cycles of anti-VEGF administration. Anti-VEGF therapy may include, for example, the administration of an anti-VEGF drug, including, for example, Aflibercept. In this embodiment, a rebounder is defined as a non-responder to anti-VEGF therapy after the first at least three cycles of anti-VEGF administration. In one embodiment, the machine learning classifier is a linear discriminant analysis (LDA) classifier trained to distinguish non-rebounders from rebounders. In another embodiment, the machine learning classifier may be another type of machine learning classifier, including a support vector machine (SVM) classifier, a quadratic discriminant analysis (QDA) classifier, a random forest classifier, or a deep learning classifier, including a convolutional neural network (CNN) trained to distinguish a positive class (e.g., non-rebounder, responder) from a negative class (e.g., rebounder, non-responder). In one embodiment, the CNN is applied directly to 2D vessel representations. The probability may, in one embodiment, include a value in the range [0, 1], for example, where a value of 1 indicates membership in a positive class (e.g., non-rebounder, and a value of 0 indicates membership in a negative class (e.g., rebounder). Other ranges may be employed. Providing the VaNgOGH descriptor to the machine learning classifier includes acquiring electronic data, reading from a computer file, receiving a computer file, reading from a computer memory, or other computerized activity not practically performed in a human mind.

Operations 100 also includes, at 180, receiving, from the machine learning classifier, a probability that the ROI is a non-rebounder. The machine learning classifier computes the probability based, at least in part, on the VaNgOGH descriptor. Receiving the probability from the machine learning classifier includes acquiring electronic data, reading from a computer file, receiving a computer file, reading from a computer memory, or other computerized activity not practically performed in a human mind.

Operations 100 also includes, at 190, generating a classification of the ROI as a non-rebounder or rebounder based, at least in part, on the probability. Generating the classification may also include classifying the patient associated with the ROI as a non-rebounder or rebounder based, at least in part, on the probability. For example, upon receiving a probability that is >0.5, the ROI may be classified as a member of a positive class (e.g., non-rebounder). Upon receiving a probability of <=0.5, the ROI may be classified as a member of a negative class (e.g., rebounder). Other classification schemes may be employed. For example, upon receiving a probability that is >=0.6, the ROI may be classified as a member of the positive class (e.g., non-rebounder). Upon receiving a probability of <=0.4, the ROI may be classified as a member of the negative class (e.g., rebounder), while upon receiving a probability that is >0.4 and <0.6, the ROI may be classified as, for example, "unknown". Generating the classification includes acquiring electronic data, reading from a computer file, receiving a computer file, reading from a computer memory, or other computerized activity not practically performed in a human mind.

Operations 100 further includes, at 192, displaying the classification. Operations 192 may also include, at 192, optionally displaying the probability, the VaNgOGH descriptor $F_V$, the first order statistics of $F_{xy}$, the feature set $F_{xy}$, the retinal vascular network, or the 2D FA image. Displaying the classification or optionally displaying the probability, the VaNgOGH descriptor $F_V$, the first order statistics of $F_{xy}$, the feature set $F_{xy}$, the retinal vascular network, or the 2D FA image may include displaying the classification or optionally displaying the probability, the VaNgOGH descriptor $F_V$, the first order statistics of $F_{xy}$, the feature set $F_{xy}$, the retinal vascular network, or the 2D FA image on a computer monitor, a smartphone display, a tablet display, or other displays. Displaying the classification or optionally displaying the probability, the VaNgOGH descriptor $F_V$, the first order statistics of $F_{xy}$, the feature set $F_{xy}$, the retinal vascular network, or the 2D FA image may also include printing the classification or the VaNgOGH descriptor $F_V$, the first order statistics of $F_{xy}$, the feature set $F_{xy}$, the retinal vascular network, or the 2D FA image. Displaying the classification or optionally displaying the VaNgOGH descriptor $F_V$, the first order statistics of $F_{xy}$, the feature set $F_{xy}$, the retinal vascular network, or the 2D FA image may also include controlling a DME classification system, a personalized medicine system, a computer assisted diagnostic (CADx) system, a UWFA system, a monitor, or other display, to display operating parameters or characteristics of a machine learning classifier, during both training and testing, or during clinical operation of the machine learning classifier. By displaying the classification, example embodiments provide a timely and intuitive way for a human pathologist or other medical practitioner to more accurately distinguish non-rebounders from rebounders in DME or RVO, thus improving on existing approaches to distinguishing non-rebounders from rebounders in DME, or for determining an anti-VEGF dosing schedule for a DME patient or an RVO patient.

In one embodiment, the retinal vascular network is further defined as comprising primary vessels, secondary vessels, and tertiary vessels. In this embodiment, features are computed for primary vasculature, secondary vasculature, and tertiary vasculature. In this embodiment, defining a feature set $F_{xy}$ may further include computing features associated with primary vessels, secondary vessels, and tertiary vessels respectively. FIG. 600 illustrates FA imagery of retinal vessel networks for a responder (e.g., non-rebounder) at 610 and 616, and of a non-responder (e.g., rebounder) at 620 and 626. Primary vessels, defined in this example as vessels originating from the center of the FA image, are illustrated in red at 611 and 621. Secondary vessels, defined as vessels branching from a primary vessel, are illustrated in green at 627. Tertiary vessels, defined as vessels branching from a second vessel, are illustrated in blue at 628.

Some portions of the detailed descriptions herein are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
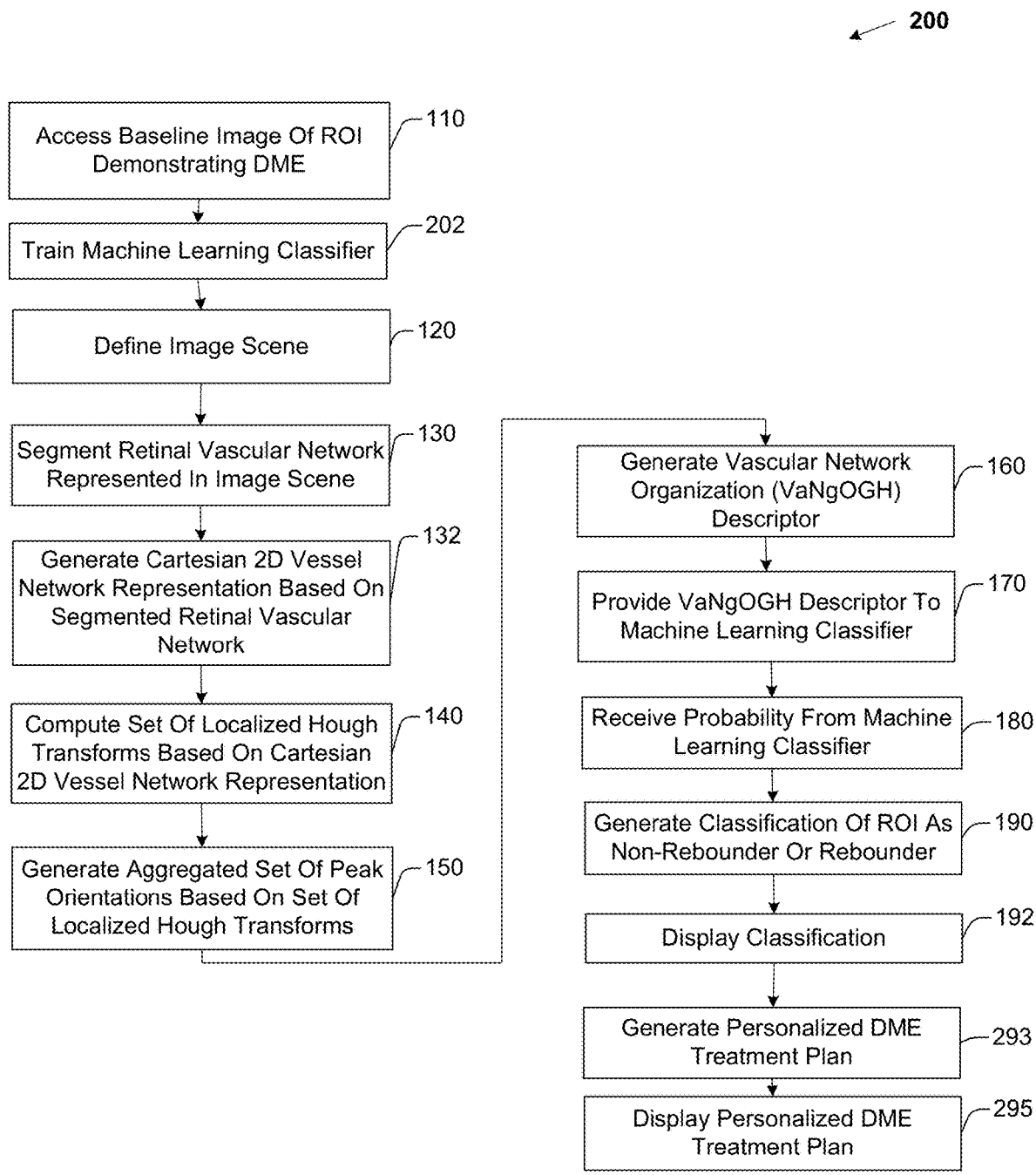
FIG. 2 is a flow diagram of example methodology or operations for distinguishing non-rebounders from rebounders based on the architectural disorder of a vascular architecture associated with DME or retinal vein occlusion (RVO) according to various embodiments described herein.

FIG. 2 is a flow diagram of example operations 200 that is similar to operations 100 but that includes additional details and elements. In this embodiment, operations 200 include, at 202, training the machine learning classifier. The machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which vascular network organization descriptor is most discriminative in distinguishing a positive class from a negative class (e.g., non-rebounder vs rebounder) or determining the optimal combination of parameters used in the computation of vascular network organization descriptors (e.g. size and stride of the sliding Hough window) to best separate a positive and negative class.

In one embodiment, upon the extraction of the VaNgOGH features from a training set of FA images, a set of 3 top features is selected using a Wilcoxon rank-sum test and used to train a linear discriminant analysis (LDA) classifier. The LDA classifier is trained and tested in a 3-fold cross-validation setting across one-hundred iterations. The locked-down model is then applied to an independent validation cohort. Performance of the LDA classifier may be assessed by the area under the receiver operating characteristic curve (AUC).

In one embodiment, training the machine learning classifier includes accessing a training dataset of FA images, where each FA image of the training dataset comprises an associated plurality of pixels, where each pixel of the associated plurality of pixels has an associated intensity. In this embodiment, training the machine learning classifier also includes computing, for each FA image of the training dataset, a VaNgOGH descriptor according to various embodiments or examples described herein. In this embodiment, training the machine learning classifier further includes training the machine learning classifier based on the training dataset, the associated values for each element of the VaNgOGH descriptor for each FA image of the training dataset, and a known prognosis associated with each FA image of the training dataset.

In one embodiment, training the machine learning classifier may optionally include testing the machine learning classifier. Testing the machine learning classifier may include accessing a testing dataset of FA images, where each FA image of the testing dataset comprises an associated plurality of pixels, where each pixel of the associated plurality of pixels has an associated intensity. Testing the machine learning classifier includes computing, for each FA image of the testing dataset, a VaNgOGH descriptor according to various embodiments described herein. Testing the machine learning classifier may further include testing the machine learning classifier based on the testing dataset, the associated values for each element of the VaNgOGH descriptor for each FA image of the testing dataset, and a known prognosis associated with each FA image of the testing dataset.

Embodiments may further include generating a personalized DME treatment plan. Operations 200 also includes, at 293, generating a personalized DME treatment plan based, at least in part, on the classification. Operations 200 may further include, in one embodiment, at 293, generating a personalized RVO treatment plan. For example, operations 200 may include, at 293 computing a first dosage or dosage schedule of a first anti-VEGF agent based, at least in part, on the classification when the ROI is classified as a member of the positive class, or a second dosage or dosage schedule of a second, different immunotherapy agent based, at least in part, on the classification when the ROI is classified as a member of the negative class. For example, for a region of tissue demonstrating DME or RVO classified as likely to rebound, a first dosage schedule may be generated, while for a region of tissue classified as unlikely to rebound (e.g., non-rebounder), a second, different dosage schedule of a different anti-VEGF agent may be generated. Different personalized treatment plans may also generate different follow-up or monitoring schedules depending on the classification. For example, an eye classified as a rebounder a may be scheduled, according to the personalized cancer treatment plan, more frequent monitoring, than an eye classified as non-rebounder. In this embodiment, operations 200 further include at 295, displaying the personalized DME treatment plan or the personalized RVO treatment plan.

Figure 10:
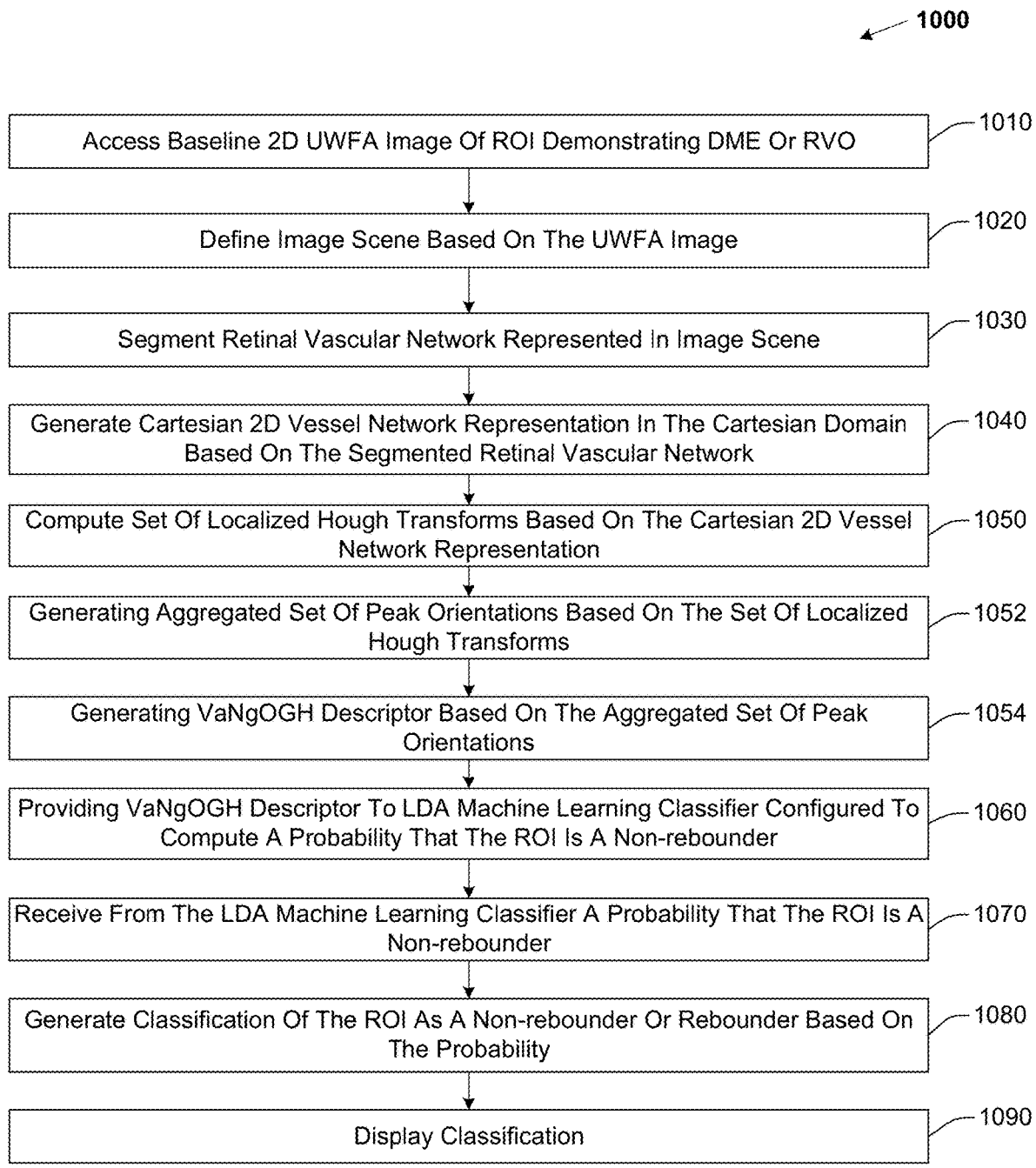
FIG. 10 is a flow diagram of example methodology or operations for distinguishing non-rebounders from rebounders based on the architectural disorder of a vascular architecture associated with DME or RVO according to various embodiments described herein.

While FIGS. 1, 2, and 10 illustrate various actions occurring in serial, it is to be appreciated that various actions illustrated in FIG. 1, FIG. 2, or FIG. 10, could occur substantially in parallel. By way of illustration, a first process could involve generating or accessing an FA image of an eye, a second process could involve generating a Cartesian 2D vessel network representation, and a third process could involve computing a Hough transform. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods or operations 100 or 200 or 1000, or any other methods or operations described herein. While executable instructions associated with the listed methods are described as being stored on a computer-readable storage device, it is to be appreciated that executable instructions associated with other example methods or operations described or claimed herein may also be stored on a computer-readable storage device. In different embodiments the example methods or operations described herein may be triggered in different ways. In one embodiment, a method or operation may be triggered manually by a user. In another example, a method or operation may be triggered automatically.

Techniques and aspects of various embodiments are further explained below, in connection with an example embodiment that facilitates distinguishing non-rebounders from rebounders for a patient represented in FA, imagery, including UWFA imagery.

Example Use Case: Distinguishing Eyes Based on Durability of Treatment Response Using Vascular Network Organization Via Hough Transform (VaNgOGH) Features An example embodiment included training a machine learning classifier to distinguish eyes based on durability of treatment response based on VaNgOGH features. In one example, a dataset comprising N=27 cases from the PERMEATE clinical trial was accessed. PERMEATE is a prospective study, at the Cleveland Clinic Foundation (CCF), for treatment-naive eyes with foveal-involving edema secondary to DME or Retinal Vein Occlusion (RVO), utilizing monthly Aflibercept injection (2 mg) for the initial 6 months. Eligibility criteria included men and women 18 years of age, foveal-involving retinal edema secondary to DME or RVO, and standardized best-corrected visual acuity of 20/25 or worse. Participants who were exposed to any prior therapy to treat DME or RVO, such as laser or pharmacotherapy, were excluded from this study. Participants were also excluded if significant vitreous hemorrhage was present which limited the ability to undergo FA and collect images of the macular or retinal periphery. All the images were collected over a span of 12 months with UWFA and OCT-A taken quarterly. Additional higher-order quantitative measurements included macular ellipsoid zone (EZ)-RPE volume, en face percentage of EZ attenuation, and volumetric analysis of retinal fluid. The intravitreal aflibercept (IAI) 2 mg was utilized monthly for the first 6 months, and then administered at months 8, 10, 11, and 12. Based on recurrence of macular edema/visual acuity worsening at visit 8 (i.e., first visit with q8 week dosing), the patients were classified into non-rebounders (N=15) and rebounders (N=12).

In this example, blood vessels represented in the UWFA imagery were segmented. In this example, the UWFA scans were evaluated utilizing a vessel, leakage, and microaneurysm segmentation technique. One suitable vessel, leakage, and microaneurysm segmentation technique is described in Ehlers, J. P., Wang, K., Vasanji, A., Hu, M., and Srivastava, S. K., "Automated quantitative characterization of retinal vascular leakage and microaneurysms in ultra-wide field fluorescein angiography," *British Journal of Ophthalmology* 101(6), 696-699 (2017). This segmentation technique generated multiple masks for additional analysis including a panretinal vascular skeletonized map, leakage localization mask, and microaneurysm mask. Other automated segmentation techniques may be employed.

Examples compute VaNgOGH features. In this example, VaNgOGH invokes Hough transformation to characterize the vessel network across multiple spatial representations. In one example, embodiments may operate both in the cartesian domain, to capture disorder in the plane of image acquisition, and in the spherical domain, to capture deflections of neighboring vasculature towards point of interest. In this example, owing to the 2D nature of the FA images, embodiments leverage the cartesian coordinate space by computing VaNgOGH of the segmented vasculature and summarize the features across regions in order to capture the magnitude of the angiogenic influence. VaNgOGH features consist of the first order statistics (mean, median, variance, skewness and kurtosis) of maximum Hough peak orientations computed in a sliding fashion across vessel projections summarizing vasculature orientation in the XY plane. Embodiments define an image scene I as I=(C,f), where I is a spatial grid C of pixels $c \in C$ in a two-dimensional (2D) space $\mathbb{R}^2$. Each pixel, $c \in C$, is associated with an intensity value f (c). $V_{xy}$ depicts the vascular network in the image plane. Using a N by N sliding window W with an offset of k pixels, each pixel in $V_{xy}$ is mapped to an accumulator space using the Hough Transform, where the equation of a line is represented by $$y = \left(-\frac{\cos\theta}{\sin\theta}\right)x + \left(\frac{\rho}{\sin\theta}\right).$$

This transforms the spatial coordinate system (x,y) to the polar coordinate system (ρ,θ) such that for every point on the medial axis representation $V_{xy}$, there exists a unique sinusoid in the Hough accumulator space. The five grid locations accumulating the most sinusoid crossings are identified for each W Feature set $F_{xy}$, then comprises the θ values associated with the five most prominent peak orientations such that $F_{xy}=[\theta_1, \theta_2, \ldots \theta_5]$. The final VaNgOGH feature set, $F_V$, is generated as a concatenation of the first order statistics, mean, median, standard deviation, skewness, and kurtosis, of $F_{xy}$.

In this example, a 25 by 1 VaNgOGH feature vector, summarizing the localized vessel orientations, is computed for each FA image. To avoid the curse of dimensionality, in this example minimum redundancy maximum relevance (mRMR) feature selection is used to select the top 3 features in a 3-fold cross-validated fashion over 100 iterations. The features are assigned scores based on their frequency of occurrence. The top 3 features in each fold and each run are used in conjunction with a linear discriminant analysis (LDA) classifier to distinguish non-rebounders from rebounders. Clinical parameters such as central subfield thickness, macular volume, and letter scores were evaluated at baseline visit. The statistical significance of these features are computed for the two groups using a Wilcoxon ranksum test. Further, the significance values are compared against the one obtained using the top discriminating vessel disorder feature.

Figure 3:
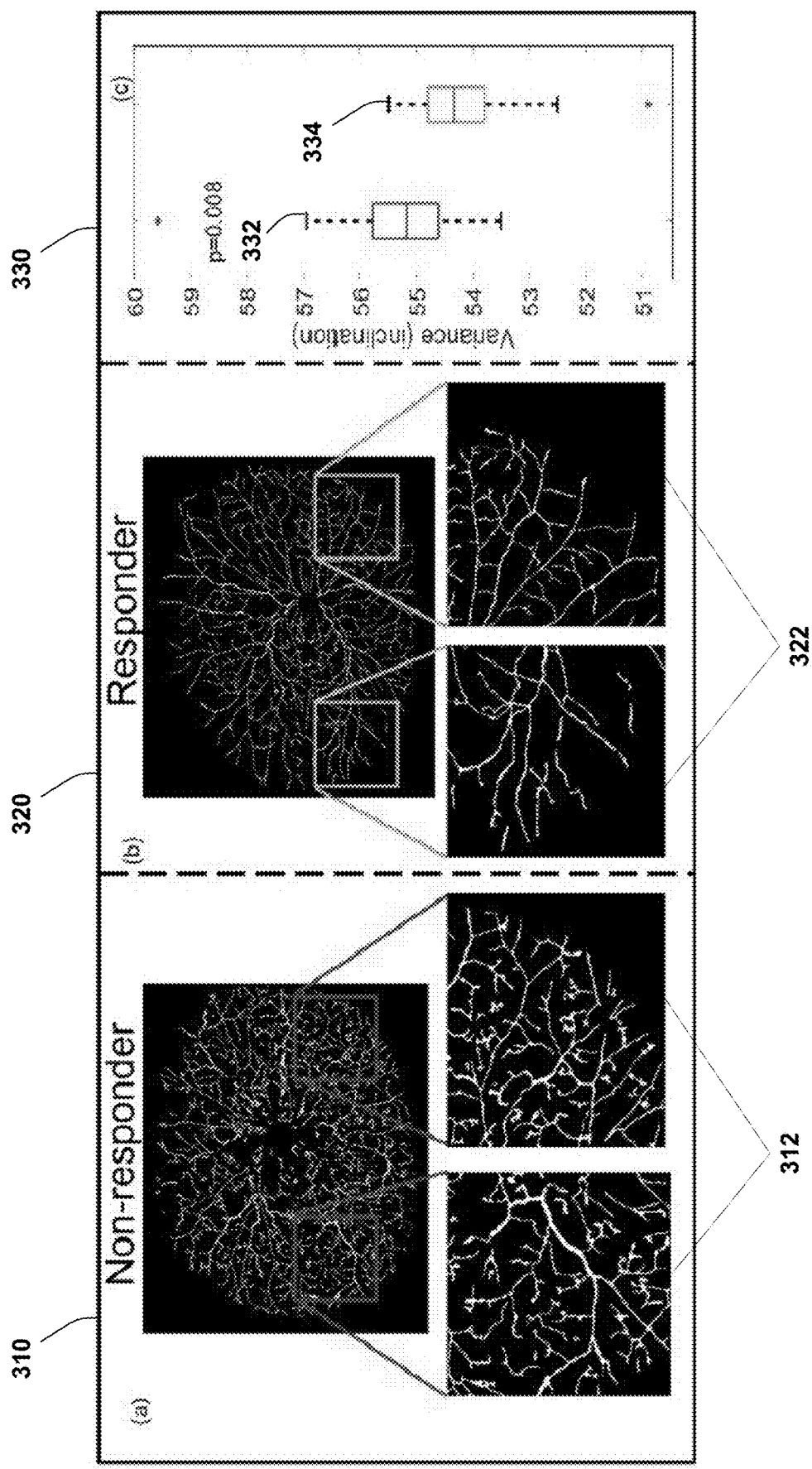
FIG. 3 illustrates vascular networks on example baseline fluorescein angiography (FA) images of eyes demonstrating DME.

Embodiments facilitate distinguishing eyes or patients associated with eyes based on durability of treatment response using VaNgOGH features. In this example, the cross-validated area under the receiver operating characteristic curve was found to be 0.73+−0.1 using the VaNgOGH descriptors, with the variance of local orientations showing a statistically significant difference (p=0.008) between the two groups of patients. FIG. 3 illustrates, at 310 and 320, the vessel network on example baseline FA images of a rebounder and a non-rebounder, respectively. Insets 312 and 322 show a zoomed-in representation of the regional vasculature. As may be observed, the vessels are more tortuous in the rebounder as compared to the non-rebounder. This is quantitatively reflected in the box and whisker plot at 330. The box plot in red 332 corresponds to the variance of vessel inclination values from the rebounders, and the box and whisker plot in green 334 corresponds to the variance of inclination values from the rebounders. As may be observed in the zoomed in insets 312 and 322, the higher density of tertiary vasculature in the rebounder results in an increased variance of local vessel orientations/inclination.

Figure 4:
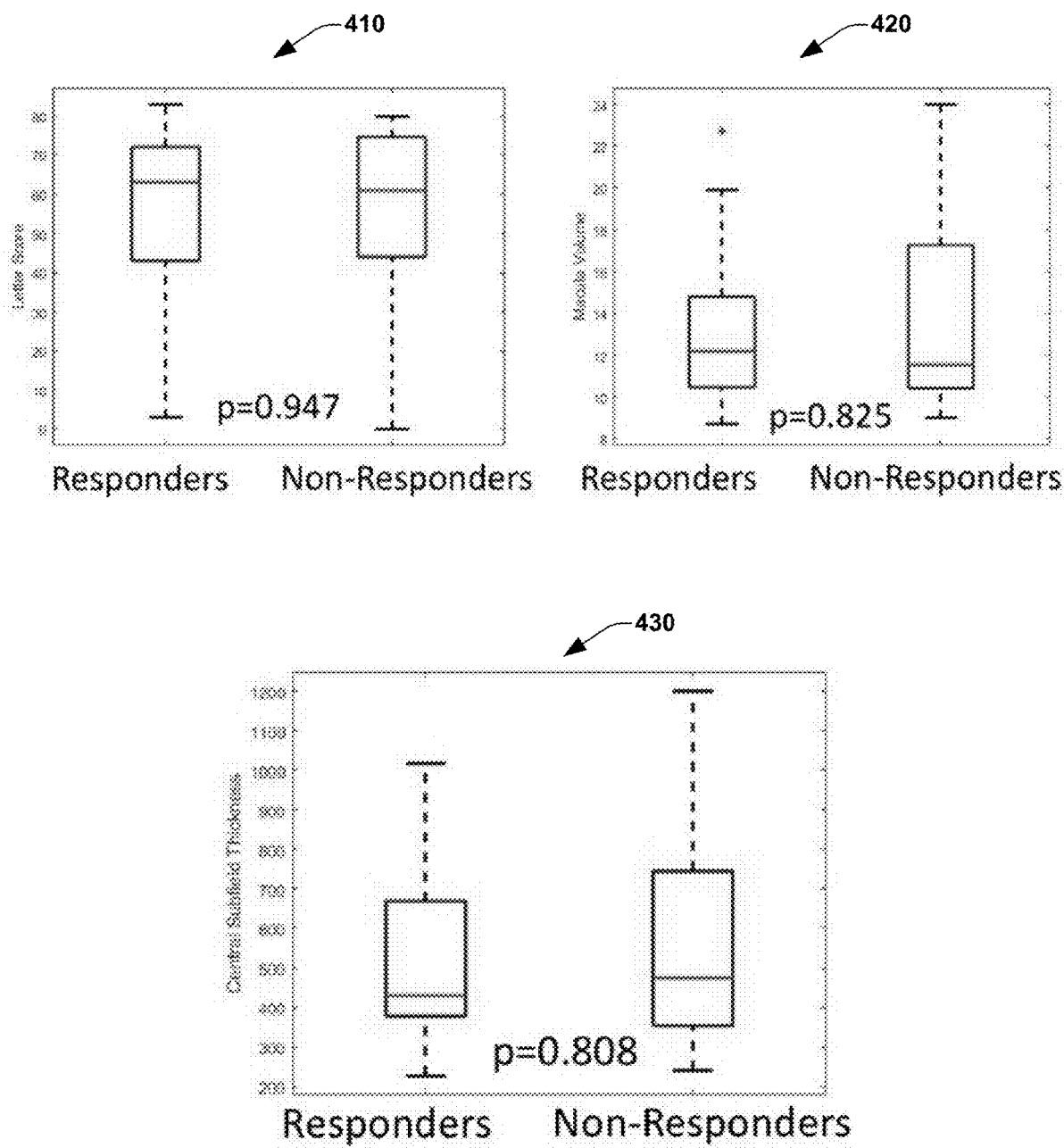
FIG. 4 illustrates box and whisker plots of baseline clinical parameters in DME.

Embodiments facilitate improved distinction of non-rebounders from rebounders compared to existing approaches. In this example, clinical parameters such as central sub-field thickness (p=0.808), macular volume (p=0.825) and letter scores (p=0.947) on baseline imaging were not found to be statistically significantly different between the rebounders and non-rebounders. FIG. 4 illustrates box and whisker plots of baseline clinical parameters. Box and whisker plot 410 illustrates a letter score baseline clinical parameter. Box and whisker plot 420 illustrates a macular volume baseline clinical parameter. Box and whisker plot 430 illustrates a central subfield thickness baseline clinical parameter.

In diabetic patients, the first major anatomical change comes in the form of the presence of long-term hyperglycemia. The elevated levels of glucose lead to a loss of vascular regulatory function. Arterioles and venules within the eye subsequently dilate and elongate. Retinal ischemia is soon followed by capillary loss, increased permeability, and retinal neovascularization. In theory, with more vascular changes, we should expect to see more dysfunction within retinal vasculature and a quicker progression of DME. Embodiments facilitate determining fundamental differences in localized vessel orientations between eyes that may tolerate more extended dosing intervals with anti-VEGF therapy compared to eyes that require more frequent dosing. Baseline vasculature disorder, as quantified by VaNgOGH according to various embodiments described herein, is higher in eyes that require more frequent dosing. Embodiments quantify characteristics of vessel curvature on pretherapy FA scans, including UWFA scans, and facilitate discriminating between candidates who may require less frequent dosing and those who may require more frequent dosing.

Examples employ a VaNgOGH descriptor, which models the architectural disorder of the retinal vascular network on baseline FA scans of patients who are subsequently treated with intravitreal aflibercept. Variance of VaNgOGH orientations on baseline UWFA are statistically significantly lower in eyes that tolerated longer dosing intervals. These fundamental differences in vessel orientations are captured in a localized fashion by VaNgOGH, and facilitate defining an imaging marker to identify potential candidates for therapy with less frequent dosing.

UWFA provides a unique window to overall disease activity compared to photos alone and identifies overall leakage burden, microaneurysms, and underlying ischemia. However, UWFA interpretation currently relies on subjective physician interpretation and quantitative higher-order assessment is not readily available. Thus, embodiments that quantify angiographic activity/severity using VaNgOGH according to various embodiments described herein, facilitate providing enhanced guidance for progression risk, need for treatment initiation, individualized treatment selection, and ongoing necessity of treatment compared to existing approaches. Embodiments further facilitate providing an improved, additive approach to existing clinical workflow, which may increase accuracy in predicting tolerance of Aflibercept or other anti-VEGF treatment, or which may decrease resources required in distinguishing patients who are non-rebounders from rebounders.

Improved identification of patients as candidates for anti-VEGF treatment, or improved classification of patients as non-rebounders or rebounders, based on a vascular network organization descriptor as described herein, may produce the technical effect of improving the administration of DME treatments or RVO treatments, including anti-VEGF treatments, by increasing the accuracy of and decreasing the time required to determine if a patient is likely to be a non-rebounder or rebounder. Treatments and resources, including expensive anti-VEGF agents may be more accurately tailored to patients with a likelihood of benefiting from said treatments and resources, so that more appropriate treatment protocols may be employed, and expensive resources are not wasted, when ROIs represented in FA images are more accurately and more quickly classified. For example, patients identified as rebounders may be spared treatment or surgical procedures, while patients identified as non-rebounders may be more effectively provided with such treatment or surgical procedures. Controlling a DME non-rebounder classification apparatus, a UWFA system, a CADx system, a personalized medicine system, or other apparatus configured to classify a DME patient or RVO patient as a non-rebounder or rebounder, or distinguish patients who will benefit from a particular anti-VEGF treatment schedule, based on improved, more accurate analysis of 2D FA images further improves the operation of the system, processor, or apparatus, since the accuracy of the system, processor, or apparatus is increased and unnecessary operations will not be performed.

Embodiments described herein, including at least operations 100 and 200, operations 1000, and apparatus 700 or 800, resolve features extracted from digitized radiological images imagery at a higher order or higher level than a human can resolve in the human mind or with pencil and paper. For example, 2D vascular disorder features in the retina that are not perceivable by the human eye may be detected by embodiments, and the VaNgOGH descriptor generated by embodiments are not properties of a tissue that are perceivable by the human eye, computable using pencil and paper, or practically computed in the human mind. Embodiments thus perform actions, steps, processes, or other actions that are not practically performed in the human mind, at least because they require a processor or circuitry to access digitized images stored in a computer memory and to extract or compute features including the generation of vascular features in Cartesian co-ordinates that are based on the digitized images and not on properties of tissue or the images that are perceivable by the human eye. Embodiments described herein use a combined order of specific rules, elements, operations, or components that render information into a specific format that is then used and applied to create desired results more accurately, more consistently, and with greater reliability than existing approaches, thereby producing the technical effect of improving the performance of the machine, computer, or system with which embodiments are implemented.

Figure 7:
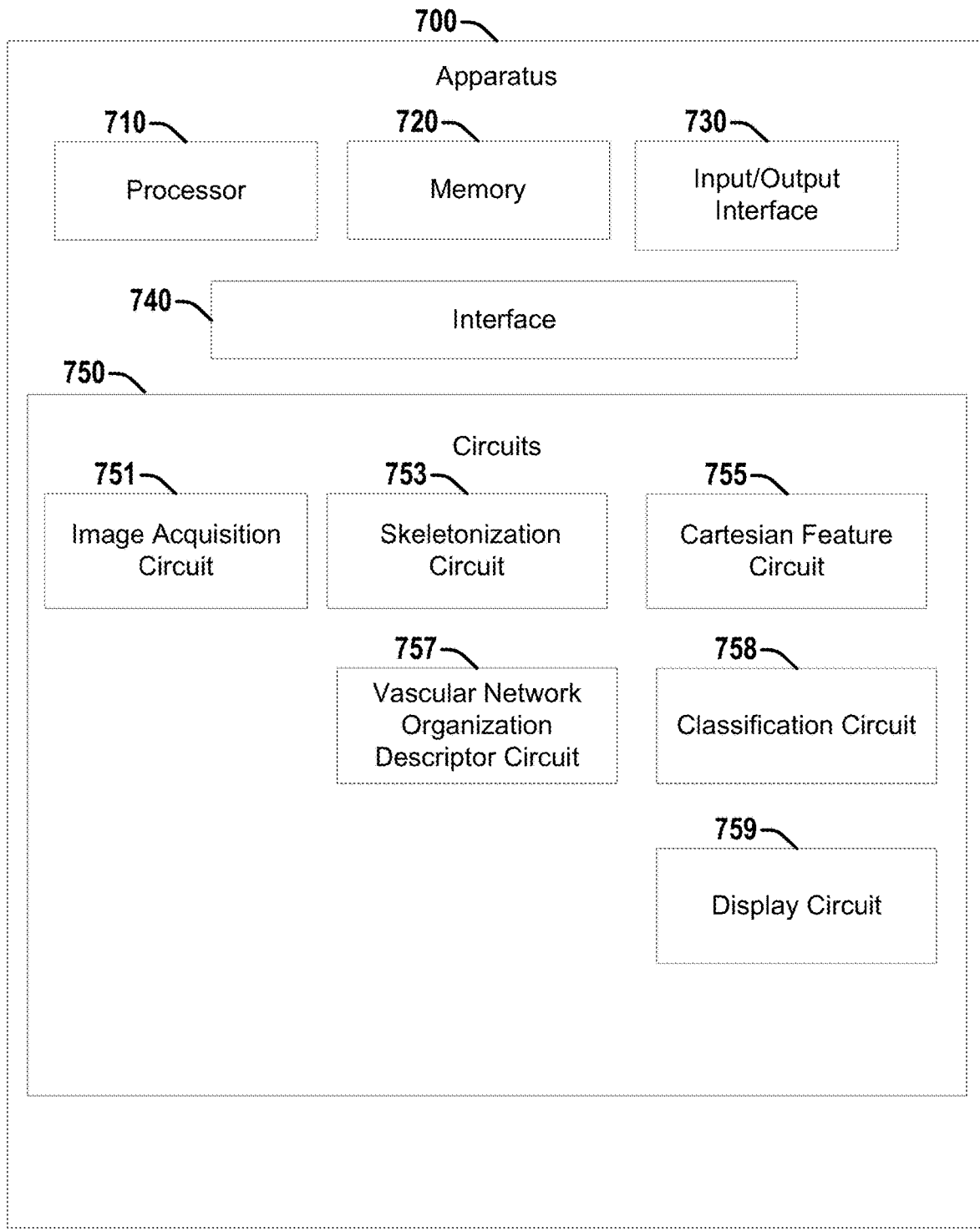
FIG. 7 illustrates an example apparatus for distinguishing non-rebounders from rebounders based on the architectural disorder of a vascular architecture associated with DME or RVO.

FIG. 7 illustrates an example apparatus 700. Apparatus 700 may be configured to generate a radiomic descriptor of retinal vascular morphology and classify a region of tissue into a positive class or a negative class based on the descriptor. Apparatus 700 includes a processor 710. Apparatus 700 also includes a memory 720. Processor 710 may, in one embodiment, include circuitry such as, but not limited to, one or more single-core or multi-core processors. Processor 710 may include any combination of general-purpose processors and dedicated processors (e.g., graphics processors, application processors, etc.). The processors may be coupled with or may include memory (e.g. memory 720) or storage and may be configured to execute instructions stored in the memory 720 or storage to enable various apparatus, applications, or operating systems to perform the operations. Memory 720 is configured to store a digitized image of a region of interest (ROI) demonstrating DME pathology or RVO pathology. The digitized image has a plurality of pixels, a pixel having an intensity.

Memory 720 may be further configured to store a training set of images demonstrating DME pathology or RVO pathology, or a testing set of images demonstrating DME pathology or RVO pathology. At least one member of the training set is classified a non-rebounder, and at least one other, different member of the training set is classified as a rebounder. At least one member of the testing set is classified as a non-rebounder, and at least one other, different member of the testing set is classified as a rebounder. Memory 720 may be further configured to store information associated with a patient associated with a member of the training or testing set of images stored in memory 720, for example, a known prognosis (e.g., non-rebounder, rebounder) associated with the patient, or clinical information associated with the patient.

Apparatus 700 also includes an input/output (I/O) interface 730, a set of circuits 750, and an interface 740 that connects the processor 710, the memory 720, the I/O interface 730, and the set of circuits 750. I/O interface 730 may be configured to transfer data between memory 720, processor 710, circuits 750, and external devices, for example, a DME eye classification system, an RVO eye classification system, a CADx system, an FA image acquisition system, an UWFA image acquisition system, an MRI system, a CT system, or a digital whole slide scanner.

The set of circuits 750 includes an image acquisition circuit 751. Image acquisition circuit 751 is configured to access an image of a region of interest (ROI). The ROI includes a plurality of pixels, a pixel having an intensity. In one embodiment, the image is a two-dimensional (2D) fluorescein angiography (FA) image of an ROI demonstrating DME. In one embodiment, the 2D FA image is an ultra-wide field FA (UWFA) image of the region of tissue demonstrating DME or RVO. The image may be a baseline (e.g., pre-anti-VEGF treatment) image. The image has a plane of acquisition z. Accessing the digitized image may include accessing a digitized image stored in memory 720. In one embodiment, accessing the digitized image may include accessing a digitized image stored in a data storage device, including a hard disk drive, a solid state device, a tape drive, or accessing a digitized image over a local area network. Accessing the digitized image includes acquiring electronic data, reading from a computer file, receiving a computer file, reading from a computer memory, or other computerized activity not practically performed in a human mind.

The set of circuits 750 also includes a skeletonization circuit 753. Skeletonization circuit 753 is configured to define an image scene based on the 2D FA image, where the image scene includes the retinal vascular network, according to various embodiments described herein. Skeletonization circuit 753 is further configured to generate a segmented retinal vascular network by segmenting the retinal vascular network represented in the image scene, according to various embodiments described herein.

The set of circuits 750 also includes a Cartesian feature circuit 755. Cartesian feature circuit 755 is configured to generate a Cartesian 2D vessel network representation in the Cartesian domain based on the segmented retinal vascular network, according to various embodiments described herein. Cartesian feature circuit 755 is also configured to compute a set of localized Hough transforms based on the Cartesian 2D vessel network representation, according to various embodiments described herein. Cartesian feature circuit 755 is further configured to generate an aggregated set of peak orientations based on the set of localized Hough transforms, according to various embodiments described herein.

The set of circuits 750 also includes a vascular network organization via Hough Transforms (VaNgOGH) descriptor circuit 757. VaNgOGH descriptor circuit 757 is configured to generate a VaNgOGH descriptor based on the aggregated set of peak orientations, according to various embodiments described herein.

The set of circuits 750 also includes a classification circuit 758. Classification circuit 758 is configured to compute a probability that the ROI is a non-rebounder based, at least in part, on the VaNgOGH descriptor using a linear discriminant analysis (LDA) machine learning approach. Classification circuit 758 is further configured to generate a classification of the ROI as a non-rebounder or rebounder based on the probability. In one embodiment, classification circuit 758 may be configured as another, different type of machine learning classifier or deep learning classifier, including, for example, a quadratic discriminant analysis (QDA) classifier, a random forests classifier, or as a convolutional neural network (CNN) classifier.

The set of circuits 750 also includes a display circuit 759. Display circuit 759 is configured to display the classification, according to various embodiments described herein.

In one embodiment, skeletonization circuit 753 is configured to segment the retinal vascular network by computing a centerline of a vessel of the retinal vascular network. Skeletonization circuit 753 is, in this embodiment, also configured to generate a skeleton S of the retinal vascular network, where S comprises a series of points in 2D Cartesian space. In this embodiment, Cartesian feature circuit 755 is configured to generate the Cartesian 2D vessel network representation by generating a 2D representation of S in the XY plane.

In one embodiment, Cartesian feature circuit 755 is configured to compute a set of localized Hough transforms by, for an N pixel by N pixel sliding window W with an offset of k pixels, mapping each pixel in the 2D representation of S in the XY plane to an accumulator space using a Hough transform of the 2D representation of S in the XY plane into polar co-ordinates $(\rho,\theta)$, such that for each point in the medial axis skeleton S there exists a unique sinusoid in the accumulator space. In this embodiment, Cartesian feature circuit 755 is also configured to identify the top five grid locations accumulating the most sinusoid crossings for each window W In this embodiment, Cartesian feature circuit 755 is further configured to generate an aggregated set of peak orientations based on the set of localized Hough transforms by computing a feature set $F_{xy}$ comprising the $\theta$ values associated with the five most prominent peak orientations such that $F_{xy}=[\theta_1, \theta_2, \ldots \theta_5]$.

In one embodiment, VaNgOGH descriptor circuit 757 is configured to generate the VaNgOGH descriptor by concatenating the mean, median, standard deviation, skewness, and kurtosis, of each element of $F_{xy}$, respectively. In one embodiment, VaNgOGH descriptor circuit 757 may be configured to compute the mean, median, standard deviation, skewness, and kurtosis, of each element of $F_{xy}$, respectively.

Figure 8:
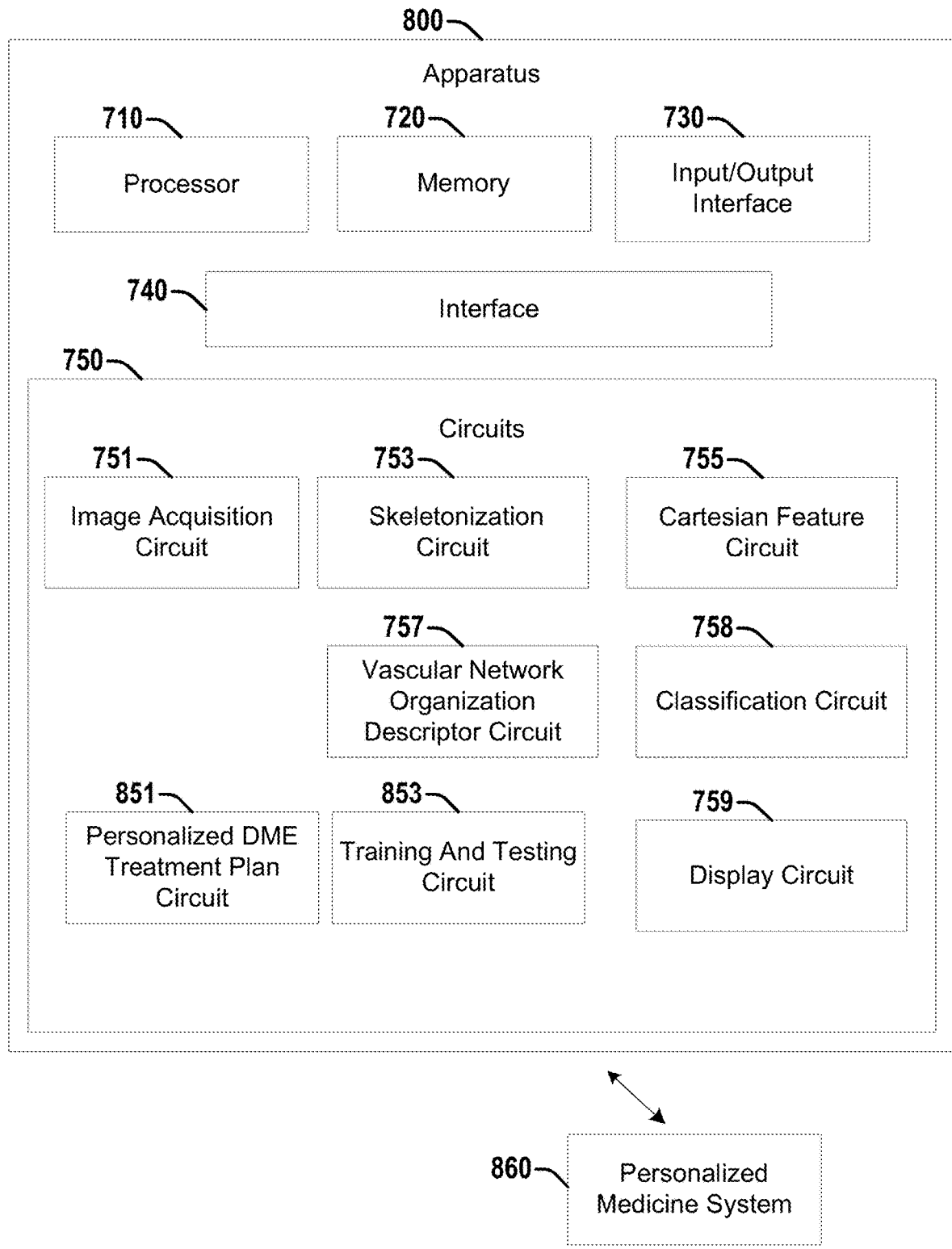
FIG. 8 illustrates an example apparatus for distinguishing non-rebounders from rebounders based on the architectural disorder of a vascular architecture associated with DME or RVO.

FIG. 8 illustrates an apparatus 800 that is similar to apparatus 700 but that includes additional elements and details. Apparatus 800 includes a personalized DME treatment plan circuit 851. Personalized DME treatment plan circuit 851 is configured to generate a personalized DME treatment plan based, at least in part, on the classification. Personalized DME treatment plan circuit 851 is also configured to optionally control the display circuit to display the personalized DME treatment plan. In one embodiment, personalized DME treatment plan circuit 851 may be configured to compute a first dosage or dosage schedule of a first anti-VEGF agent based, at least in part, on the classification when the ROI is classified as a non-rebounder (e.g., responder), or a second dosage or dosage schedule of an anti-VEGF agent based, at least in part, on the classification when the ROI is classified as a rebounder (e.g., non-responder). Different personalized treatment plans may also generate different follow-up or monitoring schedules depending on the classification. For example, an eye classified as a rebounder may be scheduled, according to the personalized DME treatment plan, a different monitoring schedule, than an eye classified as non-rebounder. In one embodiment, personalized DME treatment plan circuit 851 is further configured to generate a personalized RVO treatment plan based on the classification, and to optionally control the display circuit to display the personalized RVO treatment plan.

Apparatus 800 also includes a training and testing circuit 853. Training and testing circuit 853 is configured to train a machine learning classifier (e.g., classification circuit 758). Training and testing circuit 853 is configured to train classification circuit 758 by accessing a training dataset of FA images, where each FA image of the training dataset comprises an associated plurality of pixels, where each pixel of the associated plurality of pixels has an associated intensity. Training and testing circuit 853 is also configured to train classification circuit 758 by computing according to various embodiments described herein, or controlling VaNgOGH circuit 757 to compute, for each FA image of the training dataset, a VaNgOGH descriptor. Training and testing circuit 853 is further configured to train classification circuit 758 by training classification circuit 758 based on the training dataset, the associated values for each element of the VaNgOGH descriptor for each FA image of the training dataset, and a known prognosis associated with each FA image of the training dataset.

Training and testing circuit 853 is further configured to optionally test the classification circuit 758 by accessing a testing dataset of FA images, where each FA image of the testing dataset comprises an associated plurality of pixels, where each pixel of the associated plurality of pixels has an associated intensity. Training and testing circuit 853 is further configured to optionally test the classification circuit 758 by computing, according to various embodiments described herein, or controlling VaNgOGH circuit 757 to compute, for each FA image of the testing dataset, a VaNgOGH descriptor. Training and testing circuit 853 is further configured to optionally test the classification circuit 758 by testing the machine learning classifier based on the testing dataset, the associated values for each element of the VaNgOGH descriptor for each FA image of the testing dataset, and a known prognosis associated with each FA image of the testing dataset.

In one embodiment, display circuit 759 is further configured to optionally display at least one of the FA image, the ROI, the vasculature, the Cartesian 2D vessel network representation, the set of localized Hough transforms, the aggregated set of peak orientations, a vascular network organization descriptor, or the probability. Displaying the classification or optionally displaying at least one of the FA image, the ROI, the vasculature, the Cartesian 2D vessel network representation, the set of localized Hough transforms, the aggregated set of peak orientations, a vascular network organization descriptor, or the probability may also include printing the classification or at least one of the FA image, the ROI, the vasculature, the Cartesian 2D vessel network representation, the set of localized Hough transforms, the aggregated set of peak orientations, a vascular network organization descriptor, or the probability.

Apparatus 800 may be configured to transmit the classification, the FA image, the ROI, the vasculature, the Cartesian 2D vessel network representation, the set of localized Hough transforms, the aggregated set of peak orientations, a vascular network organization descriptor, or the probability, or other information to personalized medicine system 860. Apparatus 800 may be configured to control personalized medicine system 860 to display at least one of the classification, the radiological image, the ROI, the vasculature, the Cartesian 2D vessel network representation, the set of localized Hough transforms, the aggregated set of peak orientations, a vascular network organization descriptor, or the probability or other information. In one embodiment, personalized medicine system 860 may be configured as a member of circuits 750.

Figure 9:
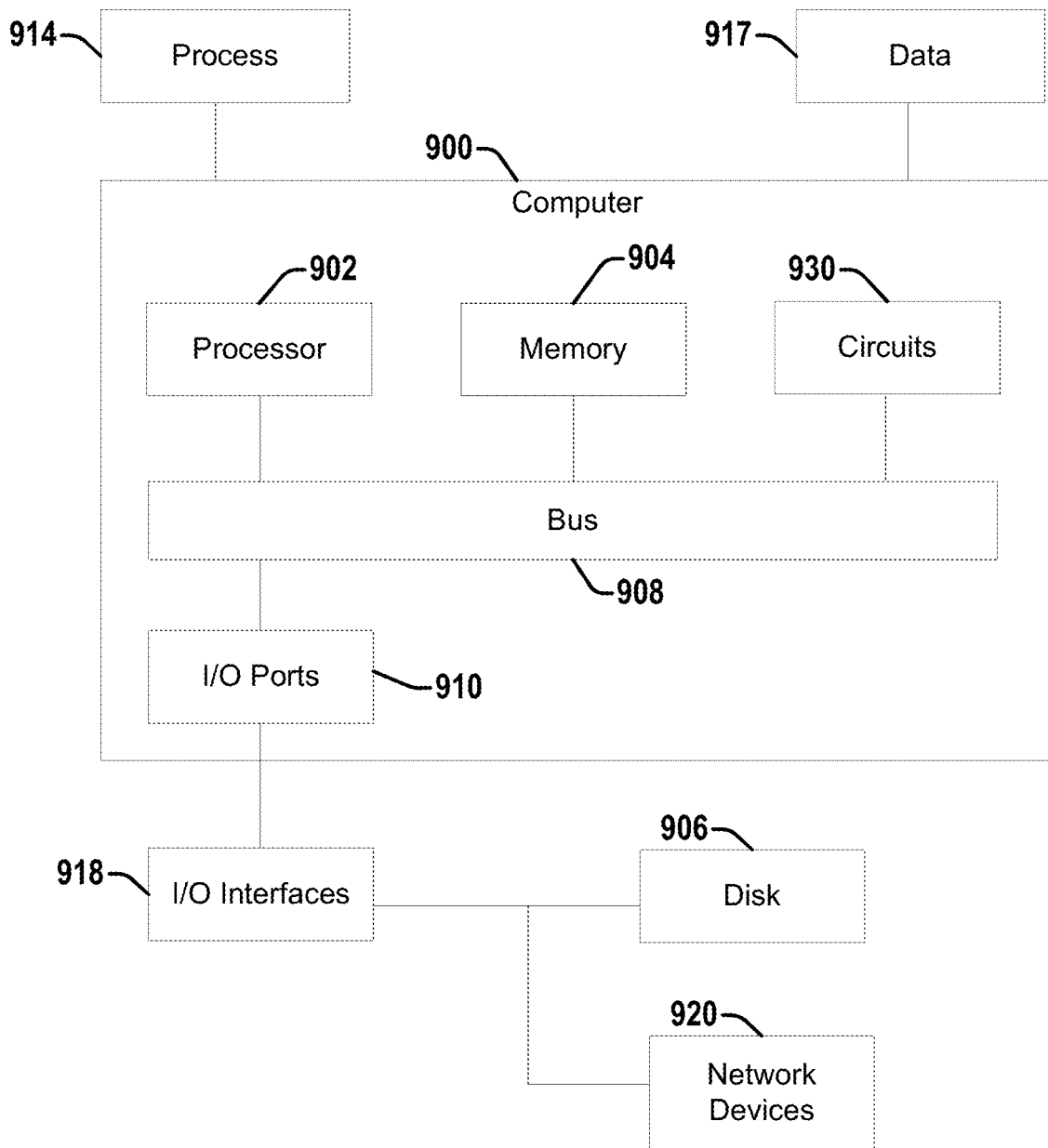
FIG. 9 illustrates an example computer in which embodiments described herein may operate.

FIG. 9 illustrates an example computer 900 in which example methods illustrated herein can operate and in which example methods, apparatus, circuits, operations, or logics may be implemented. In different examples, computer 900 may be part of a DME classification system or apparatus, an RVO classification system or apparatus, a CADx system, a UWFA system, an MRI system, a CT system, a digital whole slide scanner, or a personalized medicine system, or may be operably connectable to a DME classification system or apparatus, an RVO classification system or apparatus, a CADx system, a UWFA system, an MRI system, a CT system, a digital whole slide scanner, or a personalized medicine system.

Computer 900 includes a processor 902, a memory 904, and input/output (I/O) ports 910 operably connected by a bus 908. In one example, computer 900 may include a set of logics or circuits 930 that perform operations for or a method of distinguishing eyes based on durability of treatment response using VaNgOGH features, or classifying eyes on FA imagery, including by using a machine learning classifier. Thus, the set of circuits 930, whether implemented in computer 900 as hardware, firmware, software, and/or a combination thereof may provide means (e.g., hardware, firmware, circuits) for distinguishing eyes based on durability of treatment response using VaNgOGH features, or classifying eyes on radiological imagery. In different examples, the set of circuits 930 may be permanently and/or removably attached to computer 900.

Processor 902 can be a variety of various processors including dual microprocessor and other multi-processor architectures. Processor 902 may be configured to perform steps of methods claimed and described herein. Memory 904 can include volatile memory and/or non-volatile memory. A disk 906 may be operably connected to computer 900 via, for example, an input/output interface (e.g., card, device) 918 and an input/output port 910. Disk 906 may include, but is not limited to, devices like a magnetic disk drive, a tape drive, a Zip drive, a flash memory card, or a memory stick. Furthermore, disk 906 may include optical drives like a CD-ROM or a digital video ROM drive (DVD ROM). Memory 904 can store processes 914 or data 917, for example. Data 917 may, in one embodiment, include digitized images, including FA or UWFA images of tissue demonstrating DME or RVO. Disk 906 or memory 904 can store an operating system that controls and allocates resources of computer 900.

Bus 908 can be a single internal bus interconnect architecture or other bus or mesh architectures. While a single bus is illustrated, it is to be appreciated that computer 900 may communicate with various devices, circuits, logics, and peripherals using other buses that are not illustrated (e.g., PCIE, SATA, Infiniband, 1394, USB, Ethernet).

Computer 900 may interact with input/output devices via I/O interfaces 918 and input/output ports 910. Input/output devices can include, but are not limited to, FA systems, CT systems, MRI systems, digital whole slide scanners, an optical microscope, a keyboard, a microphone, a pointing and selection device, cameras, video cards, displays, disk 906, network devices 920, or other devices. Input/output ports 910 can include but are not limited to, serial ports, parallel ports, or USB ports.

Computer 900 may operate in a network environment and thus may be connected to network devices 920 via I/O interfaces 918 or I/O ports 910. Through the network devices 920, computer 900 may interact with a network. Through the network, computer 900 may be logically connected to remote computers. The networks with which computer 900 may interact include, but are not limited to, a local area network (LAN), a wide area network (WAN), or other networks, including the cloud.

FIG. 10 illustrates a flow diagram of an example method or set of operations 1000 for distinguishing non-rebounders from rebounders to anti-vascular endothelial growth factor (VEGF) treatment. Operations 1000 includes acquiring electronic data, reading from a computer file, receiving a computer file, reading from a computer memory, or other computerized activity not practically performed in a human mind. Operations 1000 includes, at 1010 accessing a pre-anti-VEGF treatment two-dimensional (2D) ultra-wide field FA (UWFA) image of region of interest (ROI) demonstrating diabetic macular edema (DME) or retinal vein occlusion (RVO). The UWFA image including a plurality of pixels, a pixel having an intensity. The ROI includes a retinal vascular network.

Operations 1000 also includes, at 1020, defining an image scene based on the UWFA image. The image scene includes the retinal vascular network.

Operations 1000 also includes, at 1030, segmenting the retinal vascular network represented in the image scene. The retinal vascular network may be segmented according to various embodiments described herein.

Operations 1000 also includes, at 1040, generating a Cartesian 2D vessel network representation in the Cartesian domain based on the segmented retinal vascular network. The Cartesian 2D vessel network representation may be generated according to various embodiments described herein.

Operations 1000 also includes, at 1050, computing a set of localized Hough transforms based on the Cartesian 2D vessel network representation. The set of localized Hough transforms may be computed according to various embodiments described herein.

Operations 1000 also includes, at 1052, generating an aggregated set of peak orientations based on the set of localized Hough transforms. The aggregated set of peak orientations may be generated according to various embodiments described herein.

Operations 1000 also includes, at 1054, generating a vascular network organization via Hough transform (VaNgOGH) descriptor based on the aggregated set of peak orientations. The VaNgOGH descriptor quantifies a disorder of the retinal vascular network. The VaNgOGH descriptor may be generated according to various embodiments described herein.

Operations 1000 also includes, at 1060, providing the VaNgOGH descriptor to a linear discriminant analysis (LDA) machine learning classifier configured to compute a probability that the ROI is a non-rebounder. The LDA machine learning classifier may be configured to compute the probability according to various embodiments described herein.

Operations 1000 also includes, at 1070, receiving, from the LDA machine learning classifier, a probability that the ROI is a non-rebounder. The LDA machine learning classifier computes the probability based, at least in part, on the VaNgOGH descriptor.

Operations 1000 also includes, at 1080, generating a classification of the ROI as a non-rebounder or rebounder based on the probability. The classification may be generated according to various embodiments described herein. In one embodiment, generating the classification includes classifying the ROI or the patient associated with the ROI as a non-rebounder or rebounder, or as a responder to anti-VEGF therapy, or non-responder to anti-VEGF therapy, based on the probability.

Operations 1000 further includes, at 1090, displaying the classification according to various embodiments described herein. Displaying the classification may, in one embodiment, further include optionally displaying the probability, the VaNgOGH descriptor, the aggregated set of peak orientations, the set of localized Hough transforms, the Cartesian 2D vessel network representation, the segmented vasculature, or the image.

Example 1 comprises a non-transitory computer-readable storage device storing computer-executable instructions that, in response to execution, cause a processor to perform operations, the operations comprising: accessing a two-dimensional (2D) fluorescein angiography (FA) image of a region of interest (ROI) demonstrating diabetic macular edema (DME), where the ROI includes a retinal vascular network, the image including a a plurality of pixels, a pixel having an intensity; defining an image scene based on the 2D FA image, where the image scene includes the retinal vascular network; segmenting the retinal vascular network represented in the image scene; generating a Cartesian 2D vessel network representation in the Cartesian domain based on the segmented retinal vascular network; computing a set of localized Hough transforms based on the Cartesian 2D vessel network representation; generating an aggregated set of peak orientations based on the set of localized Hough transforms; generating a vascular network organization via Hough transform (VaNgOGH) descriptor based on the aggregated set of peak orientations; providing the VaNgOGH descriptor to a machine learning classifier configured to compute a probability that the ROI is a non-rebounder based, at least in part, on the VaNgOGH descriptor; receiving, from the machine learning classifier, a probability that the ROI is a non-rebounder; generating a classification of the ROI as a non-rebounder or rebounder based on the probability; and displaying the classification.

Example 2 comprises the subject matter of any variation of any of example(s) 1, where segmenting the retinal vascular network comprises segmenting the retinal vascular network using a morphological-based segmentation technique, or a deep learning segmentation technique.

Example 3 comprises the subject matter of any variations of any of example(s) 1-2, where generating the Cartesian 2D vessel network representation comprises: computing a centerline of a vessel of the retinal vascular network; generating a skeleton S of the retinal vascular network, where S comprises a series of points in 2D Cartesian space; and generating a 2D representation of S in the XY plane.

Example 4 comprises the subject matter of any variations of any of example(s) 1-3, where computing the set of localized Hough transforms comprises: for an N pixel by N pixel sliding window W with an offset of k pixels, mapping each pixel in the 2D representation of S in the XY plane to an accumulator space using a Hough transform of the 2D representation of S in the XY plane into polar co-ordinates $(\rho, \theta)$, such that for each point in the medial axis skeleton S there exists a unique sinusoid in the accumulator space; and identifying the top five grid locations accumulating the most sinusoid crossings for each window W.

Example 5 comprises the subject matter of any variations of any of example(s) 1-4, where N=10 and k=3.

Example 6 comprises the subject matter of any variations of any of example(s) 1-5, where generating the aggregated set of peak orientations based on the set of localized Hough transforms comprises: computing a feature set $F_{xy}$ comprising the $\theta$ values associated with the five most prominent peak orientations such that $F_{xy}=[\theta_1, \theta_2, \ldots \theta_5]$.

Example 7 comprises the subject matter of any variations of any of example(s) 1-6, where the VaNgOGH descriptor comprises a concatenation of the mean, median, standard deviation, skewness, and kurtosis, of each element of $F_{xy}$, respectively.

Example 8 comprises the subject matter of any variations of any of example(s) 1-7, where the machine learning classifier is a linear discriminant analysis (LDA) classifier configured to distinguish non-rebounders from rebounders.

Example 9 comprises the subject matter of any variations of any of example(s) 1-8, where the 2D FA image is a pre-anti-vascular endothelial growth factor (VEGF) treatment ultra-wide field FA (UWFA) image of an ROI demonstrating DME.

Example 10 comprises the subject matter of any variations of any of example(s) 1-9, the operations further comprising training the machine learning classifier to distinguish non-rebounders from rebounders.

Example 11 comprises the subject matter of any variations of any of example(s) 1-10, where training the machine learning classifier comprises: accessing a training dataset of FA images, where each FA image of the training dataset comprises an associated plurality of pixels, where each pixel of the associated plurality of pixels has an associated intensity; computing, for each FA image of the training dataset, a VaNgOGH descriptor; training the machine learning classifier based on the training dataset, the associated values for each element of the VaNgOGH descriptor for each FA image of the training dataset, and a known prognosis associated with each FA image of the training dataset.

Example 12 comprises the subject matter of any variations of any of example(s) 1-11, the operations further comprising generating a personalized DME treatment plan based, at least in part, on the classification.

Example 13 comprises the subject matter of any variations of any of example(s) 1-12, the operations further comprising optionally displaying the personalized DME treatment plan.

Example 14 comprises an apparatus comprising: a processor; a memory configured to store a digitized image of a region of interest (ROI) demonstrating diabetic macular edema (DME), the digitized image having a plurality of pixels, a pixel having an intensity; an input/output (I/O) interface; a set of circuits; and an interface that connects the processor, the memory, the I/O interface, and the set of circuits, the set of circuits comprising: an image acquisition circuit configured to: access a two-dimensional (2D) fluorescein angiography (FA) image of an ROI demonstrating DME, where the ROI includes a retinal vascular network, the image including a a plurality of pixels, a pixel having an intensity; a skeletonization circuit configured to: define an image scene based on the 2D FA image, where the image scene includes the retinal vascular network; generate a segmented retinal vascular network by segmenting the retinal vascular network represented in the image scene; a Cartesian feature circuit configured to: generate a Cartesian 2D vessel network representation in the Cartesian domain based on the segmented retinal vascular network; compute a set of localized Hough transforms based on the Cartesian 2D vessel network representation; generate an aggregated set of peak orientations based on the set of localized Hough transforms; a vascular network organization via Hough Transforms (VaNgOGH) descriptor circuit configured to: generate a VaNgOGH descriptor based on the aggregated set of peak orientations; a classification circuit configured to:

compute a probability that the ROI is a non-rebounder, where the classification circuit computes the probability based, at least in part, on the VaNgOGH descriptor using a linear discriminant analysis (LDA) machine learning approach; generate a classification of the ROI as a non-rebounder or rebounder based on the probability; and a display circuit configured to display the classification.

Example 15 comprises the subject matter of any variations of any of example(s) 14, where the 2D FA image is an ultra-wide field FA (UWFA) image of an ROI demonstrating DME.

Example 16 comprises the subject matter of any variations of any of example(s) 14-15, where: the skeletonization circuit is configured to segment the retinal vascular network by computing a centerline of a vessel of the retinal vascular network, and generating a medial axis skeleton S of the retinal vascular network, where S comprises a series of points in 2D Cartesian space; and where the Cartesian feature circuit is configured to generate the Cartesian 2D vessel network representation by generating a 2D representation of S in the XY plane.

Example 17 comprises the subject matter of any variations of any of example(s) 14-16, where: the Cartesian feature circuit is configured to: compute a set of localized Hough transforms by, for an N pixel by N pixel sliding window W with an offset of k pixels, mapping each pixel in the 2D representation of S in the XY plane to an accumulator space using a Hough transform of the 2D representation of S in the XY plane into polar co-ordinates $(\rho,\theta)$, such that for each point in the medial axis skeleton S there exists a unique sinusoid in the accumulator space; and identify the top five grid locations accumulating the most sinusoid crossings for each window W; and generate an aggregated set of peak orientations based on the set of localized Hough transforms by computing a feature set $F_{xy}$ comprising the $\theta$ values associated with the five most prominent peak orientations such that $F_{xy}=[\theta_1, \theta_2, \ldots \theta_5]$; and where the VaNgOGH descriptor circuit is configured to generate the VaNgOGH descriptor by concatenating the mean, median, standard deviation, skewness, and kurtosis, of each element of $F_{xy}$, respectively.

Example 18 comprises the subject matter of any variations of any of example(s) 14-17, the set of circuits further comprising a personalized DME treatment plan circuit configured to generate a personalized DME treatment plan based, at least in part, on the classification, and to optionally control the display circuit to display the personalized DME treatment plan.

Example 19 comprises the subject matter of any variations of any of example(s) 14-18, the set of circuits further comprising a training and testing circuit configured to: access a training dataset of FA images, where each FA image of the training dataset comprises an associated plurality of pixels, where each pixel of the associated plurality of pixels has an associated intensity; control the VaNgOGH descriptor circuit to compute, for each FA image of the training dataset, a VaNgOGH descriptor; train the classification circuit based on the training dataset, the associated values for each element of the VaNgOGH descriptor for each FA image of the training dataset, and a known prognosis associated with each FA image of the training dataset; and optionally test the classification circuit by: accessing a testing dataset of FA images, where each FA image of the testing dataset comprises an associated plurality of pixels, where each pixel of the associated plurality of pixels has an associated intensity; controlling the VaNgOGH descriptor circuit to compute, for each FA image of the testing dataset, a VaNgOGH descriptor; testing the classification circuit based on the testing dataset, the associated values for each element of the VaNgOGH descriptor for each FA image of the testing dataset, and a known prognosis associated with each FA image of the testing dataset.

Example 20 comprises a non-transitory computer-readable storage device storing computer-executable instructions that, in response to execution, cause a processor to perform operations for distinguishing non-rebounders from rebounders to anti-vascular endothelial growth factor (VEGF) treatment, the operations comprising: accessing a pre-anti-VEGF treatment two-dimensional (2D) ultra-wide field FA (UWFA) image of region of interest (ROI) demonstrating diabetic macular edema (DME) or retinal vein occlusion (RVO), where the ROI includes retinal vascular network, the UWFA image including a a plurality of pixels, a pixel having an intensity; defining an image scene based on the UWFA image, where the image scene includes the retinal vascular network; segmenting the retinal vascular network represented in the image scene; generating a Cartesian 2D vessel network representation in the Cartesian domain based on the segmented retinal vascular network; computing a set of localized Hough transforms based on the Cartesian 2D vessel network representation; generating an aggregated set of peak orientations based on the set of localized Hough transforms; generating a vascular network organization via Hough transform (VaNgOGH) descriptor based on the aggregated set of peak orientations, where the VaNgOGH descriptor quantifies a disorder of the retinal vascular network; providing the VaNgOGH descriptor to a linear discriminant analysis (LDA) machine learning classifier configured to compute a probability that the ROI is a non-rebounder; receiving, from the machine learning classifier, a probability that the ROI is a non-rebounder, where the machine learning classifier computes the probability based, at least in part, on the VaNgOGH descriptor; generating a classification of the ROI as a non-rebounder or rebounder based on the probability; and displaying the classification.

Example 21 comprises a machine readable storage device that stores instructions for execution by a processor to perform any of the described operations of examples 1-20.

Example 22 comprises an apparatus comprising: a memory; and one or more processors configured to: perform any of the described operations of examples 1-20.

Examples herein can include subject matter such as an apparatus, a DME tolerance of anti-VEGF treatment prediction system or apparatus, an RVO tolerance of anti-VEGF treatment prediction system or apparatus, a personalized medicine system, a UWFA system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system distinguishing eyes based on durability of treatment response using VaNgOGH features, or classifying eyes on FA or UWFA imagery, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, in response to execution, cause a processor to perform operations, the operations comprising:

accessing a two-dimensional (2D) fluorescein angiography (FA) image of a region of interest (ROI) demonstrating diabetic macular edema (DME), where the ROI includes a retinal vascular network, the image including a plurality of pixels, a pixel having an intensity;

defining an image scene based on the 2D FA image, where the image scene includes the retinal vascular network;

segmenting the retinal vascular network represented in the image scene;

generating a Cartesian 2D vessel network representation in the Cartesian domain based on the segmented retinal vascular network;

computing a set of localized Hough transforms based on the Cartesian 2D vessel network representation;

generating an aggregated set of peak orientations based on the set of localized Hough transforms;

generating a vascular network organization via Hough transform (VaNgOGH) descriptor based on the aggregated set of peak orientations;

providing the VaNgOGH descriptor to a machine learning classifier configured to compute a probability that the ROI is a non-rebounder based, at least in part, on the VaNgOGH descriptor;

receiving, from the machine learning classifier, a probability that the ROI is a non-rebounder;

generating a classification of the ROI as a non-rebounder or rebounder based on the probability; and displaying the classification.

2. The non-transitory computer-readable storage device of claim 1, where segmenting the retinal vascular network comprises segmenting the retinal vascular network using a morphological-based segmentation technique, or a deep learning segmentation technique.

3. The non-transitory computer-readable storage device of claim 2, where generating the Cartesian 2D vessel network representation comprises:

computing a centerline of a vessel of the retinal vascular network;

generating a skeleton S of the retinal vascular network, where S comprises a series of points in 2D Cartesian space; and generating a 2D representation of S in the XY plane.

4. The non-transitory computer-readable storage device of claim 3, where computing the set of localized Hough transforms comprises:

for an N pixel by N pixel sliding window W with an offset of k pixels, mapping each pixel in the 2D representation of S in the XY plane to an accumulator space using a Hough transform of the 2D representation of S in the XY plane into polar co-ordinates $(\rho,\theta)$, such that for each point in the medial axis skeleton S there exists a unique sinusoid in the accumulator space; and identifying the top five grid locations accumulating the most sinusoid crossings for each window W.

5. The non-transitory computer-readable storage device of claim 4, where N=10 and k=3.

6. The non-transitory computer-readable storage device of claim 4, where generating the aggregated set of peak orientations based on the set of localized Hough transforms comprises:

computing a feature set $F_{xy}$ comprising the θ values associated with the five most prominent peak orientations such that $F_{xy}=[θ_1, θ_2, \ldots θ_5]$.

7. The non-transitory computer-readable storage device of claim 6, where the VaNgOGH descriptor comprises a concatenation of the mean, median, standard deviation, skewness, and kurtosis, of each element of $F_{xy}$, respectively.

8. The non-transitory computer readable storage device of claim 1, where the machine learning classifier is a linear discriminant analysis (LDA) classifier configured to distinguish non-rebounders from rebounders.

9. The non-transitory computer readable storage device of claim 1, where the 2D FA image is a pre-anti-vascular endothelial growth factor (VEGF) treatment ultra-wide field FA (UWFA) image of an ROI demonstrating DME.

10. The non-transitory computer readable storage device of claim 1, the operations further comprising training the machine learning classifier to distinguish non-rebounders from rebounders.

11. The non-transitory computer-readable storage device of claim 10, where training the machine learning classifier comprises:
accessing a training dataset of FA images, where each FA image of the training dataset comprises an associated plurality of pixels, where each pixel of the associated plurality of pixels has an associated intensity;
computing, for each FA image of the training dataset, a VaNgOGH descriptor;
training the machine learning classifier based on the training dataset, the associated values for each element of the VaNgOGH descriptor for each FA image of the training dataset, and a known prognosis associated with each FA image of the training dataset.

12. The non-transitory computer readable storage device of claim 1, the operations further comprising generating a personalized DME treatment plan based, at least in part, on the classification.

13. The non-transitory computer readable storage device of claim 12, the operations further comprising optionally displaying the personalized DME treatment plan.

14. An apparatus comprising:
a processor;
a memory configured to store a digitized image of a region of interest (ROI) demonstrating diabetic macular edema (DME), the digitized image having a plurality of pixels, a pixel having an intensity;
an input/output (I/O) interface;
a set of circuits; and
an interface that connects the processor, the memory, the I/O interface, and the set of circuits, the set of circuits comprising:
an image acquisition circuit configured to:
access a two-dimensional (2D) fluorescein angiography (FA) image of an ROI demonstrating DME, where the ROI includes a retinal vascular network, the image including a a plurality of pixels, a pixel having an intensity;
a skeletonization circuit configured to:
define an image scene based on the 2D FA image, where the image scene includes the retinal vascular network;
generate a segmented retinal vascular network by segmenting the retinal vascular network represented in the image scene;
a Cartesian feature circuit configured to:
generate a Cartesian 2D vessel network representation in the Cartesian domain based on the segmented retinal vascular network;
compute a set of localized Hough transforms based on the Cartesian 2D vessel network representation;
generate an aggregated set of peak orientations based on the set of localized Hough transforms;
a vascular network organization via Hough Transforms (VaNgOGH) descriptor circuit configured to:
generate a VaNgOGH descriptor based on the aggregated set of peak orientations;
a classification circuit configured to:
compute a probability that the ROI is a non-rebounder, where the classification circuit computes the probability based, at least in part, on the VaNgOGH descriptor using a linear discriminant analysis (LDA) machine learning approach;
generate a classification of the ROI as a non-rebounder or rebounder based on the probability; and
a display circuit configured to display the classification.

15. The apparatus of claim 14, where the 2D FA image is an ultra-wide field FA (UWFA) image of an ROI demonstrating DME.

16. The apparatus of claim 14, where:
the skeletonization circuit is configured to segment the retinal vascular network by computing a centerline of a vessel of the retinal vascular network, and generating a medial axis skeleton S of the retinal vascular network, where S comprises a series of points in 2D Cartesian space; and where
the Cartesian feature circuit is configured to generate the Cartesian 2D vessel network representation by generating a 2D representation of S in the XY plane.

17. The apparatus of claim 16, where:
the Cartesian feature circuit is configured to:
compute a set of localized Hough transforms by, for an N pixel by N pixel sliding window W with an offset of k pixels, mapping each pixel in the 2D representation of S in the XY plane to an accumulator space using a Hough transform of the 2D representation of S in the XY plane into polar co-ordinates (ρ,θ), such that for each point in the medial axis skeleton S there exists a unique sinusoid in the accumulator space; and
identify the top five grid locations accumulating the most sinusoid crossings for each window W; and
generate an aggregated set of peak orientations based on the set of localized Hough transforms by computing a feature set $F_{xy}$ comprising the θ values associated with the five most prominent peak orientations such that $F_{xy}=[θ_1, θ_2, \ldots θ_5]$; and where
the VaNgOGH descriptor circuit is configured to generate the VaNgOGH descriptor by concatenating the mean, median, standard deviation, skewness, and kurtosis, of each element of $F_{xy}$, respectively.

18. The apparatus of claim 14, the set of circuits further comprising a personalized DME treatment plan circuit configured to generate a personalized DME treatment plan based, at least in part, on the classification, and to optionally control the display circuit to display the personalized DME treatment plan.

19. The apparatus of claim 14, the set of circuits further comprising a training and testing circuit configured to:
access a training dataset of FA images, where each FA image of the training dataset comprises an associated plurality of pixels, where each pixel of the associated plurality of pixels has an associated intensity;

control the VaNgOGH descriptor circuit to compute, for each FA image of the training dataset, a VaNgOGH descriptor;

train the classification circuit based on the training dataset, the associated values for each element of the VaNgOGH descriptor for each FA image of the training dataset, and a known prognosis associated with each FA image of the training dataset; and optionally test the classification circuit by:

accessing a testing dataset of FA images, where each FA image of the testing dataset comprises an associated plurality of pixels, where each pixel of the associated plurality of pixels has an associated intensity;

controlling the VaNgOGH descriptor circuit to compute, for each FA image of the testing dataset, a VaNgOGH descriptor;

testing the classification circuit based on the testing dataset, the associated values for each element of the VaNgOGH descriptor for each FA image of the testing dataset, and a known prognosis associated with each FA image of the testing dataset.

20. A non-transitory computer-readable storage device storing computer-executable instructions that, in response to execution, cause a processor to perform operations for distinguishing non-rebounders from rebounders to anti-vascular endothelial growth factor (VEGF) treatment, the operations comprising:

accessing a pre-anti-VEGF treatment two-dimensional (2D) ultra-wide field FA (UWFA) image of region of interest (ROI) demonstrating diabetic macular edema (DME) or retinal vein occlusion (RVO), where the ROI includes retinal vascular network, the UWFA image including a a plurality of pixels, a pixel having an intensity;

defining an image scene based on the UWFA image, where the image scene includes the retinal vascular network;

segmenting the retinal vascular network represented in the image scene;

generating a Cartesian 2D vessel network representation in the Cartesian domain based on the segmented retinal vascular network;

computing a set of localized Hough transforms based on the Cartesian 2D vessel network representation;

generating an aggregated set of peak orientations based on the set of localized Hough transforms;

generating a vascular network organization via Hough transform (VaNgOGH) descriptor based on the aggregated set of peak orientations, where the VaNgOGH descriptor quantifies a disorder of the retinal vascular network;

providing the VaNgOGH descriptor to a linear discriminant analysis (LDA) machine learning classifier configured to compute a probability that the ROI is a non-rebounder;

receiving, from the machine learning classifier, a probability that the ROI is a non-rebounder, where the machine learning classifier computes the probability based, at least in part, on the VaNgOGH descriptor;

generating a classification of the ROI as a non-rebounder or rebounder based on the probability; and displaying the classification.

* * * * *

UNITED STATES PATENT AND TRADEMARK OFFICE
CERTIFICATE OF CORRECTION

PATENT NO. : 10,970,838 B2
APPLICATION NO. : 16/415184
DATED : April 6, 2021
INVENTOR(S) : Anant Madabhushi et al.

Page 1 of 1

It is certified that error appears in the above-identified patent and that said Letters Patent is hereby corrected as shown below:

In the Specification

Column 1, Lines 16 through 21; please replace "This invention was made with government support under the grant(s) CA199374, CA202752, CA208236, EY022947, and RR012463 awarded by the National Institutes of Health. Also grants W81XWH-18-1-0404, W81XWH-13-1-0418, and W81XWH-14-1-0323 awarded by the Department of Defense. The government has certain rights in the invention." with --This invention was made with government support under RR012463, CA199374, CA216579, CA220581, CA202752, CA208236, EY022947 awarded by the National Institutes of Health and W81XWH-18-1-0404, W81XWH-13-1-0418, W81XWH-14-1-0323 awarded by the Department of Defense. The government has certain rights in the invention.--

Signed and Sealed this
Twelfth Day of July, 2022

Katherine Kelly Vidal
*Director of the United States Patent and Trademark Office*